United States Patent [19]

Essery et al.

[11] 3,985,740

[45] Oct. 12, 1976

[54] 7-[D-(α-AMINO-α-PHENYL-, 2-THIENYL- AND 3-THIENYLACETAMIDO)]-3-(5-METHYLTHIAZOL-2-YL)CARBONYLTHIOMETHYL-3-CEPHEM-4-CARBOXYLIC ACIDS

[75] Inventors: John Michael Essery; Lee Cannon Cheney, both of Fayetteville, N.Y.

[73] Assignee: Bristol-Myers Company, New York, N.Y.

[22] Filed: July 26, 1974

[21] Appl. No.: 492,123

[52] U.S. Cl.............................. 260/243 C; 260/299; 260/302 R; 424/245; 424/246
[51] Int. Cl.²......................................... C07D 501/36
[58] Field of Search ................... 260/243 CN, 243 C

[56] References Cited
UNITED STATES PATENTS

| | | | |
|---|---|---|---|
| 3,743,644 | 7/1973 | Essery et al..................... | 260/243 C |
| 3,821,207 | 6/1974 | Chow et al...................... | 260/243 C |

*Primary Examiner*—Nicholas S. Rizzo
*Assistant Examiner*—David E. Wheeler
*Attorney, Agent, or Firm*—David M. Morse

[57] ABSTRACT

7-[D-(α-Amino-α-phenyl-, 2-thienyl- and 3-thienylacetamido)]-3-(thiazol-2-yl)carbonylthiomethyl-3-cephem-4-carboxylic acid and 7-[D-(α-amino-α-phenyl-, 2-thienyl- and 3-thienylacetamido)]-3-(5-methylthiazol-2-yl)carbonylthiomethyl-3-cephem-4-carboxylic acid and their pharmaceutically acceptable salts are valuable as antibacterial agents, as nutritional supplements in animal feeds, as agents for the treatment of mastitis in cattle and as therapeutic agents in poultry and animals, including man. The compounds are especially useful in the treatment, particularly by oral administration, of infectious diseases caused by many Gram-positive and Gram-negative bacteria. Also included within the invention are easily cleavable esters of the above acids and pharmaceutically acceptable acid addition salts of said esters.

32 Claims, No Drawings

7-[D-(α-AMINO-α-PHENYL-, 2-THIENYL- AND 3-THIENYLACETAMIDO)]-3-(5-METHYL-THIAZOL-2-YL)CARBONYLTHIOMETHYL-3-CEPHEM-4-CARBOXYLIC ACIDS

BACKGROUND OF THE INVENTION

1. Field of the Invention

The cephalosporins of the present invention possess the usual attributes of such compounds and are particularly useful in the treatment of bacterial infections by oral administration.

2. Description of the Prior Art

A. Cephalosporins in General

Cephalothin and cephaloridine are well-known antibacterial agents; see U.S. Pat. Nos. 3,218,318, 3,449,338 and 3,498,979. The literature also contains considerable data on the activity of cephaloglycin and cephalexin; see U.S. Pat. Nos. 3,303,193, 3,507,861 and 3,560,489 and Great Britain Pat. Nos. 985,747 and 1,054,806. Newer cephalosporins include cefazolin and cephapirin; see U.S. Pat. No. 3,516,997 [and also Netherlands 68/05179 (Farmdoc 34,328) and South Africa 68/4513] and U.S. Pat. No. 3,422,100.

The literature on cephalosporins has been reviewed by E. P. Abraham, Quart, Rev. (London) 21, 231 (1967) by E. Van Heyningen, Advan. Drug Res., 4, 1–70 (1967) and briefly in Annual Reports in Medicinal Chemistry, Academic Press, Inc., 111 Fifth Avenue, New York, N.Y. 10003, by L. C. Cheney on pages 96 and 97 (1967) and by K. Gerzon and R. B. Morin on pages 90–93 (1968) and by Gerzon on pages 79–80 (1969) and by L. H. Conover on pages 101–102 (1970). New cephalosporins are frequently reported at the annual Interscience Conference on Antimicrobial Agents and Chemotherapy as illustrated by Sassiver et al., Antimicrobial Agents and Chemotherapy —1968, American Society for Microbiology, Bethesda, Md., pages 101–114 (1969) and by Nishida et al., ibid, 236–242 (1970). Two excellent reviews are The Cephalosporins; Microbiological, Chemical and Pharmacological Properties and Use in Chemotherapy of Infection, L. Weinstein and K. Kaplan, Annals of Internal Medicine, 72, 729–739 (1970) and Structure Activity Relationships Among Semisynthetic Cephalosporins, M. L. Sassiver and A. Lewis, Advances in Applied Microbiology, edited by D. Perlman, 13, 163–236 (1970), Academic Press, N.Y. Two more recent reviews are β-Lactam Antibiotics: Their Physicochemical Properties and Biological Activities in Relation to Structure, J. P. Hou and J. W. Poole, J. Pharmaceutical Sciences, 60(4), 503–532 (April, 1971) and Chemistry of Cephalosporin Antibiotics, R. B. Morin and B. G. Jackson, Fortschr. Chem. Org. Naturst, 28, 343–403 (1970) which includes a section on nucleophilic displacement of the acetate group at pages 370–373.

The preparation of various 7-[α-aminoarylacetamido]- cephalosporanic acids and the corresponding desacetoxy compounds in which aryl represents unsubstituted or substituted phenyl or 2- or 3-thienyl is described, for example, in British Specification Nos. 985,747, 1,017,624, 1,054,806 and 1,123,333, in Belgium Pat. No. 696,026 (Farmdoc No. 29,494), in U.S. Pat. Nos. 3,311,621, 3,352,858, 3,489,750, 3,489,751, 3,489,752, 3,518,260 and 3,575,969, in Japanese Pat. No. 16871/66 (Farmdoc 23,231), by Spencer et al., J. Med. Chem., 9(5), 746–750 (1966), by Ryan et al., J. Med Chem., 12, 310–313 (1969) and by Kurita et al., J. Antibiotics (Tokyo) (A) 19, 243–249 (1966) and see also U.S. Pat. No. 3,485,819. British Specification No. 1,073,530 includes a disclosure of the preparation of such compounds by acylation of silylated 7-ACA.

Netherlands Pat. Nos. 68/11676 (Farmdoc 36,349) and 68/12382 (Farmdoc 36,496) and U. S. Pat. Nos. 3,489,750 and 3,489,751 disclose ring-substituted cephaloglycins.

B. 3-Thiomethylcephalosporins

Various cephalosporins, including cephalosporin C on occasion but not cephaloglycin, have been reacted with nucleophilic, aromatic mercaptans to produce compounds having the structure

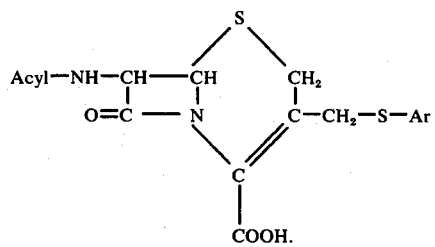

In U.S. Pat. No. 3,278,531 Ar is phenyl or certain substituted phenyls or certain aromatic heterocyclic rings named, for example, in column 5. Similar nucleophiles, e.g. 2-mercaptopyrimidines, are disclosed in U.S. Pat. No. 3,261,832 and Great Britain No. 1,101,422 and U.S. Pat. Nos. 3,479,350 and 3,502,665, all issued to Glaxo. A parallel disclosure is found in Great Britain No. 1,109,525 to Ciba, e.g. in definition "h" for $R_3$. Additional nucleophiles of this type were disclosed by Fujisawa In Belgium Pat. No. 714,518 (Farmdoc 35,307; Netherlands Pat. No. 68/06129 and South Africa Pat. No. 2695/68), in Canada Pat. No. 818,501 (Farmdoc 38,845), in Great Britain Pat. No. 1,187,323 (Farmdoc 31,936; Netherlands Pat. No. 67,14888), in U.S. Pat. No. 3,530,123 and in U.S. Pat. No. 3,516,997 (Farmdoc 34,328; Netherlands Pat. No. 68/05179) which includes the compound named cefazolin, which has a tetrazolylacetyl sidechain on the 7-amino group and a 5-methyl-thiadiazolylthiomethyl group at the 3-position and is described at some length in the scientific literature, e.g. in Antimicrobial Agents and Chemotherapy — 1969, American Society for Microbiology, Bethesda, Md. at pages 236–243 and in J. Antibiotics (Japan) 23(3), 131–148 (1970).

Replacement of the 3-acetoxy group of a cephalosporin by various heterocyclic thiols has been disclosed in U.S. Pat. No. 3,563,983 and in Netherlands Pat. No. 70/05519 (Farmdoc 80,188R) where the sidechains were, for example, 7-α-aminophenylacetamido and typical heterocyclic thiols were 2-methyl-1,3,4-thiadiazole-5-thiol and 1-methyl-1,2,3,4-tetrazole-5-thiol.

Various cephalosporins having the structure

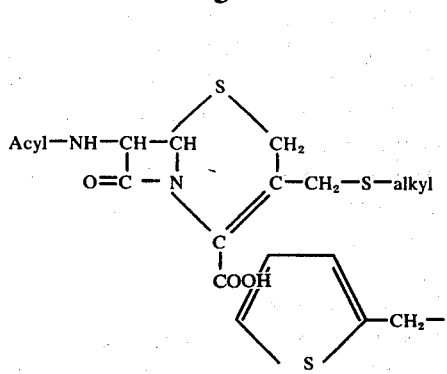

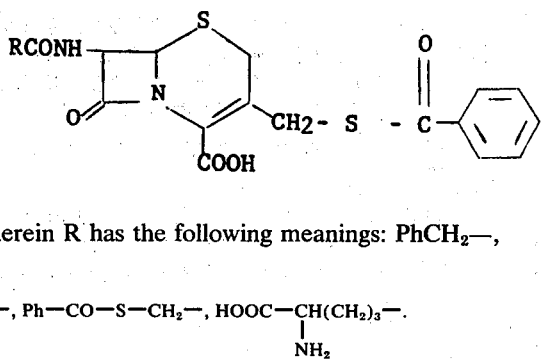

wherein R has the following meanings: PhCH₂—,

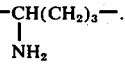

CH₂—, CH₃—S—CH₂—, Ph—CO—S—CH₂—, HOOC—CH(CH₂)₃—.
                                              |
                                             NH₂

3. Glaxo's U.S. Pat. No. 3,261,832 discloses compounds having the structure

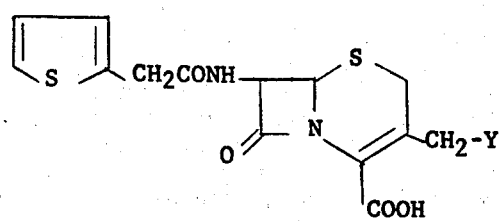

in which acyl represents various sidechains including α-aminophenylacetyl have been described in some of the above and by Glaxo in Belgium Pat. No. 734,532 (Farmdoc 41,619) and in Belgium Pat. No. 734,533 (Farmdoc 41,620) and by Lilly in Belgium Pat. No. 743,754 (Farmdoc 41,150R).

Cephalosporins having the structure

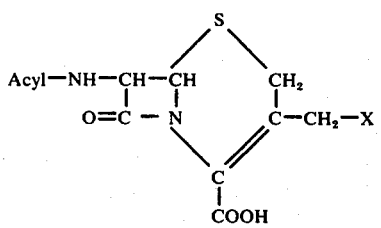

where X includes

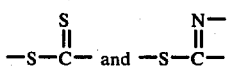

are disclosed in many patents including some of the above and in U.S. Pat. Nos. 3,239,516, 3,239,515, 3,243,435, 3,258,461, 3,431,259, 3,446,803, 3,278,531, 3,261,832 and 3,573,298.

Related publications in the scientific literature include J. Med. Chem. 8, 174–181 (1965) and J. Chem. Soc. (London) 1595–1605 (1965), 5015–5031 (1965) and 1959–1963 (1967).

C. 3-Acylthiomethylcephalosporins

The following publications and patents disclose certain additional 7-ACA derivatives containing a 3-acylthiomethyl moiety (in which phenyl is abbreviated as Ph):

1. G. F. H. Green, J. E. Page, and S. E. Staniforth, J. Chem. Soc., 1595–605 (1965). This reference gives the proton magnetic resonance spectra of the 3-benzoylthiomethyl derivative of cephalothin.

Cocker et al., J. Chem. Soc., 1142–1151 (1966) adds thiopicolinyl and references Belgium Pat. No. 650,444.

2. J. D. Cocker, et al., J. Chem. Soc., 5015–31 (1965) discloses compounds having the structure wherein Y has, for example, the following meanings:

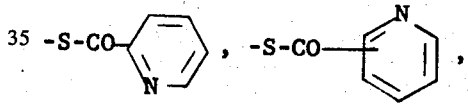

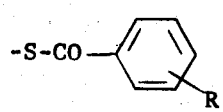

where R is CH₃O-, -NO₂, -CN, CH₃S-,

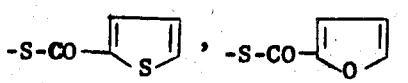

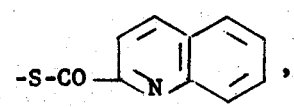

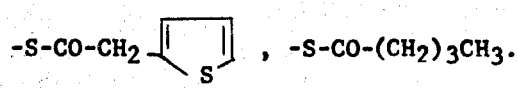

Equivalents are Netherlands Pat. No. 64/08066 (Farmdoc 15534) and Great Britain Pat. No. 1,101,424.

4. Glaxo's Netherlands Pat. No. 65/06818 (Farmdoc 19,306) discloses the reaction

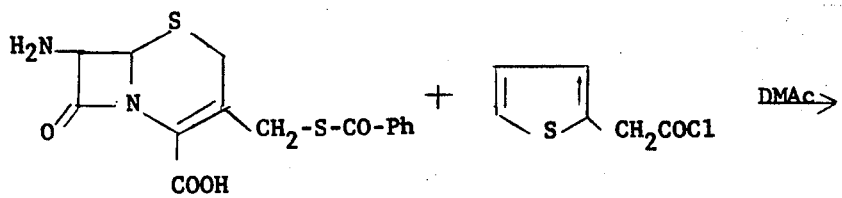

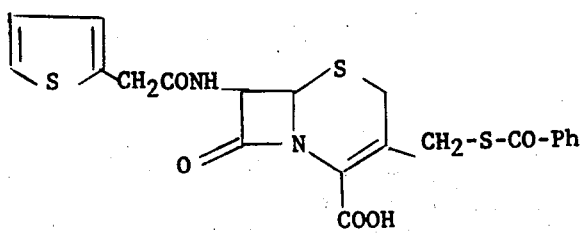

An equivalent is U.S. Pat. No. 3,502,665.

3. Glaxo's Netherlands Pat. No. 64/11521 [Chem. Abstr., 63: 13,281d (1965)] discloses the reaction

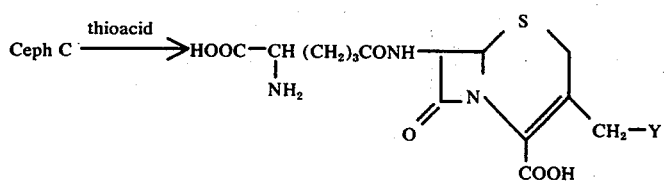

wherein Y = —S—CO—Ph or

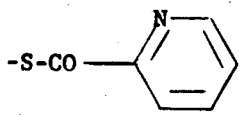

Equivalents are Great Britain Pat. No. 1,101,422 and Canada Pat. No. 796,747 (Farmdoc 17362).

6. Ciba's U.S. Pat. No. 3,555,017 discloses compounds having the structure

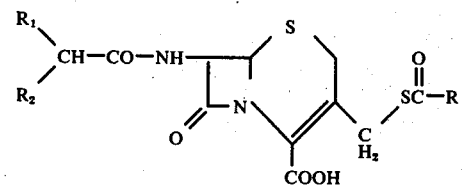

$R_1$ and $R_2$ = halogen.

As usual in Ciba's patents directed primarily to novel sidechains at the 3-position, the R group above is defined broadly as the residue of a carboxylic acid and may be illustrated by phenyl, as the residue of thiobenzoic acid. Equivalents are Belgium Pat. No. 708,241 (Farmdoc 33,276), Great Britain Pat. No. 1,211,747 and French Pat. No. 1,575,554.

7. Ciba's British Pat. No. 1,211,718 discloses compounds having the structure

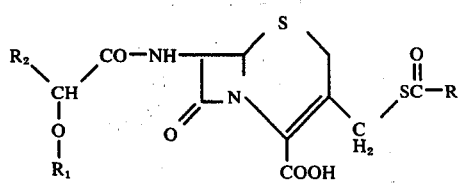

R as in 6 above.

Equivalents are Belgium Pat. No. 708,311 (Farmdoc 33,277) and U.S. Pat. No. 3,557,104.

8. Ciba's Belgium Pat. No. 751,526 (Farmdoc 90,178R) discloses compounds having the structure

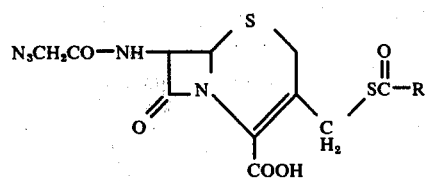

R as in 6 above.

An equivalent is Netherlands Pat. No. 70/08237.

9. Ciba's South Africa Pat. No. 69/8436 discloses compounds having the structure

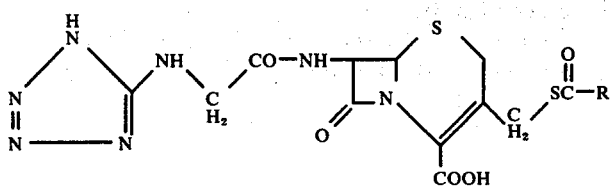

R as in 6 above.

Equivalents are Belgium Pat. No. 743,014 (Farmdoc 43,126R) and Netherlands Pat. No. 69/18611.

10. Ciba's South Africa Pat. No. 69/8399 discloses compounds having the structure

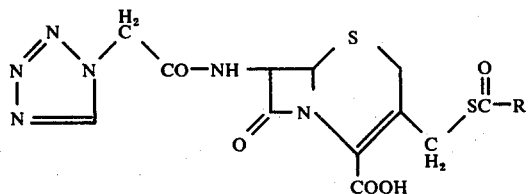

R as in 6 above.

Equivalents are Belgium Pat. No. 742,933 (Farmdoc 41,568R) and Netherlands Pat. No. 69/18531.

11. Ciba's South Africa Pat. No. 68/8185 discloses compounds having the structure

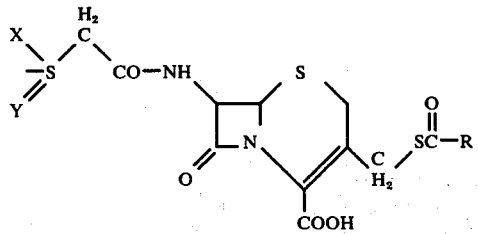

R as in 6 above.

An equivalent is Netherlands Pat. No. 68/18868.

12. Ciba's Netherlands Pat. No. 68/18868 discloses compounds having the structure

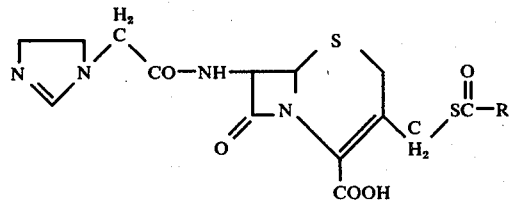

R as in 6 above.

Equivalents are South Africa Pat. No. 8120/68, German Pat. No. 1,817,121 and Belgium Pat. No. 726,316.

13. Fujisawa's Great Britain Pat. No. 1,187,323, for example, at page 5, lines 67–71 discloses compounds having the structure

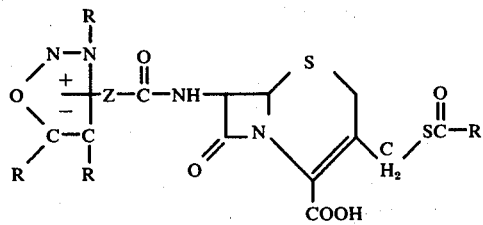

in which R represents methyl, thienyl, pyridyl, etc. and wherein general disclosure is made of other heterocyclic groups as at pages 1 and 2.

Equivalents are Netherlands Pat. No. 67/14888 (Farmdoc 13,936) and U.S. Pat. No. 3,530,123.

14. Fujisawa's Belgium Pat. No. 714,518 (Farmdoc 35,307) discloses (among many others) compounds having the structure

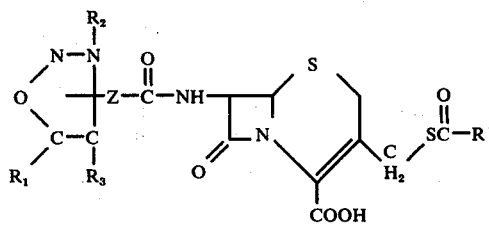

wherein R is as 13 above.

Equivalents are Netherlands Pat. No. 68/06129 and South African Pat. No. 2695/68.

15. Glaxo's U.S. Pat. No. 3,243,435 and Belgium Pat. No. 650,444 (Farmdoc 15,535) disclose generally a vast variety of compounds having the structure

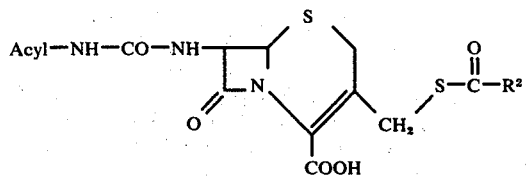

wherein $R^2$, is defined, e.g. in columns 1 and 4, to include various heterocyclic groups.

16. Ciba's South Africa Pat. No. 65/6950 (Farmdoc 22,192) discloses compounds having the structure

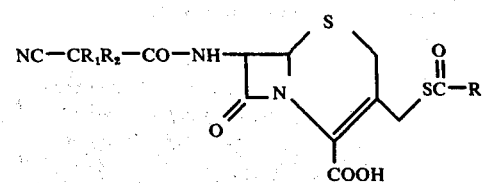

in which R in Example 20 is phenyl.

Equivalents are Great Britain Pat. No. 1,109,525 and Canada Pat. No. 807,651.

17. Glaxo's U.S. Pat No. 3,479,350 discloses a process for producing 3-pyridiniummethyl cephalosporins which utilizes as an intermediate compounds of the type described in references 2 and 3 above.

18. Ciba's U.S. Pat. No. 3,757,013 discloses compounds of the formula

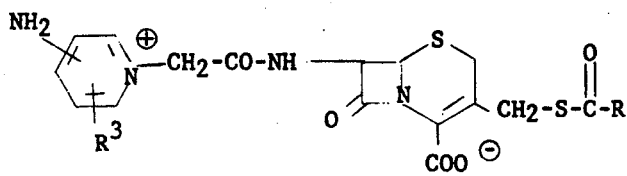

wherein $R^3$ is (lower) alkyl and R is as in 6 above.

19. Bristol's Belgian Pat. No. 795,811 (U.S. Pat. No. 3,743,644) discloses compounds of the general formula

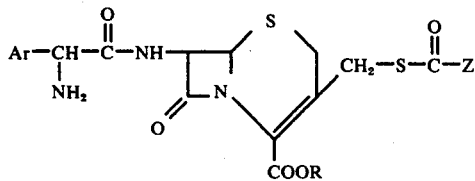

wherein Ar is phenyl, 2-thienyl or 3-thienyl; R is hydrogen, pivaloyloxymethyl, acetoxymethyl, methoxymethyl, acetonyl or phenacyl; and Z is

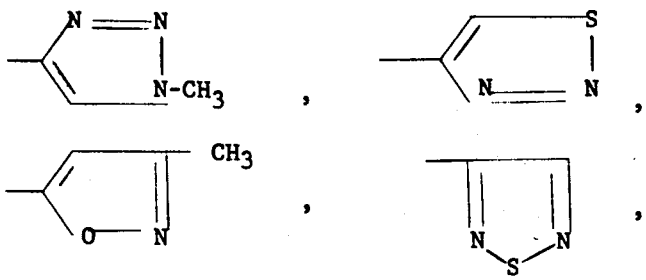

3-isothiazolyl, 4-isothiazolyl or 5-isothiazolyl.

SUMMARY OF THE INVENTION

This invention comprises the compounds having the D-configuration in the 7-sidechain and the formula

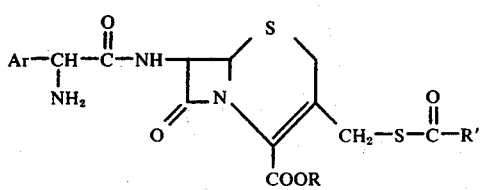

Ia wherein Ar is phenyl, 2-thienyl or 3-thienyl; R' is hydrogen, pivaloyloxymethyl, acetoxymethyl, methoxymethyl, acetonyl or phenacyl; and R' is 2-thiazolyl or 5-methyl-2-thiazolyl; and their pharmaceutically acceptable salts.

The pharmaceutically acceptable salts referred to above include the nontoxic carboxylic acid salts when R is hydrogen, e.g. nontoxic metallic salts such as sodium, potassium, calcium and aluminum, the ammonium salt and salts with nontoxic amines, e.g. trialkylamines, procaine, dibenzylamine, N-benzyl-β-phenethylamine, 1-ephenamine, N,N'-dibenzylethylenediamine, N-alkylpiperidine and other amines which have been used to form salts of penicillins. Also included within the definition of pharmaceutically acceptable salts are the nontoxic acid addition salts (amine salts) of the acids and esters of Formula Ia, e.g. salts with mineral acids such as hydrochloric, hydrobromic, hydroiodic, phosphoric and sulfuric and salts with organic acids such as maleic, acetic, citric, oxalic, succinic, benzoic, tartaric, fumaric, mandelic, ascorbic and malic.

Preferred compounds of the present invention are the compounds having the D-configuration in the 7-sidechain and the formula

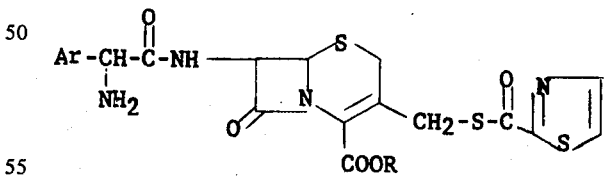

Ib wherein Ar is phenyl, 2-thienyl or 3-thienyl and R is hydrogen, pivaloyloxymethyl, acetoxymethyl, methoxymethyl, acetonyl or phenacyl; and the pharmaceutically acceptable salts thereof. Preferred compounds of formula Ib are those in which Ar is phenyl. An especially preferred compound of formula Ib is that in which Ar is phenyl and R is hydrogen; or the sodium or potassium salt thereof.

More preferred compounds of the present invention are the compounds having the D-configuration in the 7-sidechain and the formula

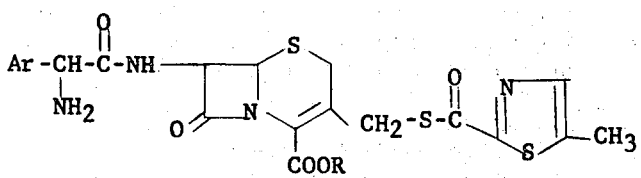

Ic wherein Ar is phenyl, 2-thienyl or 3-thienyl and R is hydrogen, pivaloyloxymethyl, acetoxymethyl, methoxymethyl, acetonyl or phenacyl; and the pharmaceutically acceptable salts thereof. Preferred compounds of formula Ic are those in which Ar is phenyl. An especially preferred compound of formula Ic is that in which Ar is phenyl and R is hydrogen; or the sodium or potassium salt thereof.

Also included in this invention are the compounds (used as either intermediates or metabolic precursors) in which the amino group is "blocked" by substituents such as t-butoxycarbonyl, carbobenzyloxy, formyl, o-nitrophenylsulfenyl, β,β,β-trichloroethoxycarbonyl, 4-oxo-2-pentenyl-2, 1-carbomethoxy-1-propenyl-2 and the like. Particularly included in such blocking groups are the ketones (especially acetone) and the aldehydes (especially formaldehyde and acetaldehyde) disclosed for example in U.S. Pat. Nos. 3,198,804 and 3,347,851 and the β-ketoesters and the β-diketones disclosed for example in U.S. Pat. No. 3,325,479 and the β-ketoamides disclosed in Japan Pat. No. 71/24714. 14.

The present invention also includes a process for the preparation of a compound having the formula

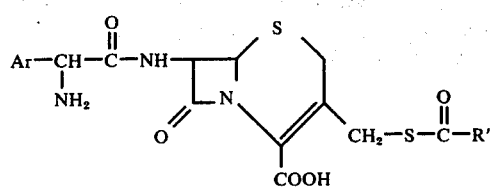

wherein Ar is phenyl, 2-thienyl or 3-thienyl; R' is 2-thiazolyl or 5-methyl-2-thiazolyl; and easily cleavable esters and pharmaceutically acceptable salts thereof; which process comprises either A. reacting a compound of the formula

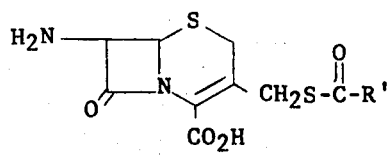

II wherein R' is as defined above or an easily cleavable ester or salt thereof with an acylating derivative of an acid having the formula

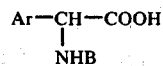 III wherein B is an amino-protecting group and Ar is as defined above and removing said aminoprotecting group B to produce the desired compound of formula I or an easily cleavable ester or pharmaceutically acceptable salt thereof and, if desired, either before or after removal of protecting group B (a) converting by methods known per se the product in the form of the free acid or salt thereof to a corresponding easily cleavable ester or pharmaceutically acceptable salt thereof or (b) converting by methods known per se the product in the form of an easily cleavable ester or salt thereof to the corresponding free acid compound or pharmaceutically acceptable salt thereof; or B. reacting a compound of the formula

wherein Ar is as defined above or an easily cleavable ester or salt thereof with a heteroaromatic thiolcarboxylic acid of the formula

 V wherein R' is as defined above or a salt thereof to form a compound of formula I or an easily cleavable ester or pharmaceutically acceptable salt thereof and, if desired, (a) converting by methods known per se the product in the form of the free acid or salt thereof to a corresponding easily cleavable ester or pharmaceutically acceptable salt thereof or (b) converting by methods known per se the product in the form of an easily cleavable ester or salt thereof to the corresponding free acid compound or pharmaceutically acceptable salt thereof.

The easily cleavable esters referred to above include ester groups which are removable by methods, e.g. chemical or enzymatic hydrolysis, which do not result in any appreciable destruction of the remaining portion of the cephalosporin molecule. Examples of suitable esters include those disclosed in U.S. Pat. Nos. 3,284,451 and 3,249,622 and U.K. Pat. Nos. 1,229,453 and 1,073,530. Particularly preferred esters are the pivaloyloxymethyl, acetoxymethyl, methoxymethyl, acetonyl and phenacyl esters.

In one method of preparing the novel cephalosporin compounds of the present invention, a 3-thiolated-7-aminocephalosporanic acid compound of formula II or an easily cleavable ester or salt of said acid or ester is acylated with the appropriate acylating derivative of formula III.

The 3-thiolated-7-aminocephalosporanic acid intermediate of formula II may be prepared by displacement of the 3-acetoxy group of 7-aminocephalosporanic acid or a salt thereof with the appropriate heteroaromatic thiolcarboxylic acid or a salt thereof. The displacement of an ester group with a thiol group is a known reaction and is preferably accomplished in aqueous solution at a temperature of at least room temperature and preferably within the range of about 50° to 100° C. in the presence of a mild base such as sodium bicarbonate.

The claimed compounds may then be obtained by acylation according to known methods of the 7-amino group of intermediate II with the acylating agent of formula III.

Because of the low solubility of the compounds of formula II in common aqueous and non-aqueous solvents, intermediate II is preferably converted prior to the acylation reaction to an easily cleavable ester or acid addition salt thereof. The procedures for preparing such esters are disclosed in the literature and are well-known to those skilled in the art of penicillin and cephalosporin chemistry. One preferred method especially useful for preparing the most preferred easily hydrolyzed esters, i.e. the pivaloyloxymethyl, acetoxymethyl, methoxymethyl, acetonyl and phenacyl esters, is disclosed in U.S. Pat. No. 3,284,451. This reference describes the esterification of sodium cephalothin with the appropriate active chloro or bromo compound (e.g. phenacyl bromide, chloroacetone, chloromethyl methyl ether, pivaloyloxymethyl chloride, acetoxymethyl chloride) followed by enzymatic removal of the thienylacetic acid sidechain. In another good method the triethylamine salt of 7-aminocephalosporanic acid is reacted directly with the active halogen compound as in U.K. patent No. 1,229,453. The compound of formula II may also be converted to a silyl ester as by the methods described in the literature, e.g. U.S. Pat. No. 3,249,622. The silyl ester group may be removed following the acylation reaction by hydrolysis or alcoholysis.

Prior to acylation reaction the amino group of acylating agent III is protected by a conventional amino-protecting group B which may be readily removed at the conclusion of the reaction. Examples of suitable amino-protecting groups include t-butoxycarbonyl, carbobenzyloxy, 2-hydroxy-1-naphthcarbonyl, trichloroethoxycarbonyl, 2-ethoxycarbonyl-1-methylvinyl and 2-methoxycarbonyl-1-methylvinyl. A particularly valuable blocking groups is a proton, as in the compound of the formula

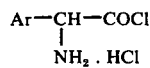

wherein Ar is phenyl, 2-thienyl or 3-thienyl. The preferred amino-protecting groups are t-butoxycarbonyl, the proton and a β-diketone or a β-ketoester as in U.K. patent No. 1,123,333 or U.S. Pat. Nos. 3,325,479 and 3,316,247, e.g. methyl acetoacetate, or a β-ketoamide as in Japan Pat. No. 71/24714. When the t-butoxycarbonyl, β-ketoester, β-diketone or β-ketoamide protecting groups are employed, it is preferred to convert the acylating acid containing the blocked amino group to a mixed anhydride, e.g. with ethyl or isobutyl chloroformate, before reaction with compound II or an ester or salt thereof. After the acylation coupling reaction, the amino-protecting group B may be removed by methods known per se to form the desired product of formula I. Thus, for example, the t-butoxycarbonyl group may be removed by use of formic acid, the carbobenzyloxy group by catalytic hydrogenation, the 2-hydroxy-1-naphthcarbonyl group by acid hydrolysis, the trichloroethoxycarbonyl group by treatment with zinc dust in glacial acetic acid, the proton by neutralization, etc. Obviously other functionally equivalent blocking groups for an amino group can be used and such groups are considered within the scope of this invention.

Acylation of a 7-amino group of a cephalosporin is a well-known reaction and any of the functional equivalents of formula III commonly used as acylating agents for primary amino groups may be employed. Examples of suitable acylating derivatives of the free acid include the corresponding acid anhydrides, mixed anhydrides, e.g. alkoxyformic anhydrides, acid halides, acid azides, active esters and active thioesters. The free acid may be coupled with compound II after first reacting said free acid with N,N'-dimethylchloroformiminium chloride or by the use of enzymes or of an N,N'-carbonyldiimidazole or an N,N'-carbonylditriazole or a carbodiimide reagent, e.g. N,N'-diisopropylcarbodiimide. N,N'-dicyclohexylcarbodiimide or N-cyclohexyl-N'-(2-morpholinoethyl)carbodiimide or of alkylylamine reagent or of an isoxazolium salt reagent. Another equivalent of the free acid is a corresponding azolide, i.e., an amide of the corresponding acid whose amide nitrogen is a member of an quasiaromatic five membered ring containing at least two nitrogen atoms, i.e., imidazole, pyrazole, the triazoles, benzimidazole, benzotriazole and their substituted derivatives. Another reactive derivative of the phenylglycine acid of formula III is the N-carboxy anhydride (Leuch's anhydride). In this structure the group which activates the carboxyl group also serves to protect the amino group. A particularly preferred acylating agent is the acid chloride hydrochloride of the formula

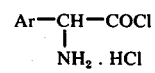

which also serves a dual function of carboxyl activation and amino protection. Mention was made above of the use of enzymes to couple the free acid with its blocked amino group with compound II. Included in the scope of such processes are the use of an ester, e.g. the methyl ester, of that free acid with enzymes provided by various microorganisms, e.g. those described by T. Takahashi et al., *J. Amer. Chem. Soc.*, 94(11), 4035–4037 (1972) and by T. Nara et al., *J. Antibiotics* (Japan), 24(5), 321–323 (1971) and in West Germany Pat. No. 2,216,113.

The particular process conditions, e.g. temperature, solvent, reaction time, etc. selected for the acylation coupling reaction are determined by the nature of the acylation method used and are known to those skilled in the art. Generally it is useful to add an organic tertiary amine, e.g. triethylamine, N,N-dimethylaniline, ethylpiperidine, 2,6-lutidine or quinoline, to serve as a proton acceptor or salt-forming agent. A preferred method illustrated in the examples which follow involves formation of a silyl ester, e.g. with trimethylchlorosilane, of the intermediate of formula II and acylation of this silylated intermediate in dry methylene chloride at a temperature of below room temperature and preferably about 0° C. with the appropriate chloride hydrochloride acylating agent of formula III in the presence of an organic tertiary amine.

At the conclusion of the acylation reaction, the acylated intermediate is subjected to aqueous hydrolysis to provide the desired cephalosporin product.

The compounds of the present invention may be isolated in any of the ways customarily employed for the isolation of similar cephalosporins. Thus, the product may be obtained as the neutral molecule, although this is probably more accurately represented as the zwitterion, or it may be isolated as a salt. Formation of the desired pharmaceutically acceptable carboxylic acid or acid addition salt is carried out by known methods, e.g. reaction of the acid with an appropriate base or acid.

At the conclusion of the acylation reaction the product obtained may be converted (before or after removal of the amino-protecting group) by methods known per se to another desired product of formula I. Thus, the compound of formula I in the form of the free acid or a salt thereof may be converted by known methods to a corresponding easily cleavable ester or pharmaceutically acceptable salt thereof. Similarly, the product of formula I in the form of an easily cleavable ester or salt thereof may be converted to the free acid product or pharmaceutically acceptable salt thereof by removal of the esterifying group, e.g. by aqueous or enzymatic hydrolysis (as with human or animal serum) or acidic or alkaline hydrolysis or by catalytic hydrogenation or by treatment with sodium thiophenoxide as taught in U.s. Pat. No. 3,284,451.

In another method of preparing the compounds of the present invention, 7-aminocephalosporanic acid or a salt thereof is acylated with the acid of formula III or an acylating derivative thereof to form a 7-acylated cephalosporin compound of the formula

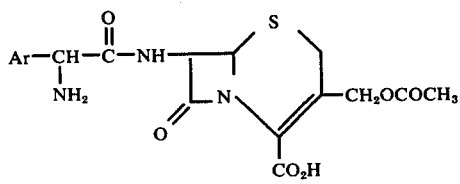

IV

Compound IV in the form of the free acid or an easily cleavable ester or salt thereof is then reacted according to the process of the present invention with a heterocyclic thiolcarboxylic acid of formula V or a salt thereof, most preferably the sodium or potassium salt. The displacement reaction is preferably conducted in aqueous solution at temperatures of about 50° C. or higher in an inert atmosphere, e.g. under nitrogen. The product of the displacement reaction may, if desired, be converted to a pharmaceutically acceptable salt by treatment with an appropriate acid or base. As in the case of the alternate process described above for preparation of the compounds of formula I, the product in the form of the free acid or salt thereof may be converted to a corresponding easily cleavable ester or pharmaceutically acceptable salt thereof or, alternatively, the product in the form of an easily cleavable ester or salt thereof may be converted to the free acid or pharmaceutically acceptable salt thereof.

The easily cleavable esters of the compound of formula I are useful as intermediates in the production of the free acid product. The pivaloyloxymethyl, acetoxymethyl and methoxymethyl esters are also useful as active antibacterial agents since on oral administration they are rapidly hydrolyzed to the active metabolite. These three esters are of particular interest because they provide on oral administration different rates and amounts of absorption and give differing concentrations of the active antibacterial agent in blood and tissues.

The preferred and most active compounds of the present invention are those having the D-configuration at the α-carbon atom in the 7-sidechain, that is, those made from D-(—)-2-phenylglycine, which is also called D-(—)-α-aminophenylacetic acid, and D-(—)-2-thienylglycine and D-(—)-3-thienylglycine. In addition, the configuration at the two optically active asymmetric centers in the β-lactam nucleus is that found in cephalosporin C produced by fermentation and in the 7-aminocephalosporanic acid derived therefrom.

The pharmaceutically active compounds of the present invention are potent antibacterial agents useful in the treatment of infectious diseases in poultry and animals, including man, caused by many Gram-positive and Gram-negative bacteria. The active compounds are also of value as nutritional supplements in animal feeds and as agents for the treatment of mastitis in cattle. The preferred compounds have also been unexpectedly found to be efficiently absorbed upon oral administration.

Despite the synthesis of a large number of cephalosporins reported in the scientific and patent literature, the only cephalosporin at the present time having sufficient activity and oral absorption for general oral use is cephalexin. In our search for new orally active cephalosporins, we have found that the compounds claimed in the present invention surprisingly and unexpectedly possess good oral absorption and at the same time appear to be superior to cephalexin in their activity against certain important pathogenic organisms. This combination of good oral absorption and high antibacterial activity in a cephalosporin while highly desirable is quite uncommon in compounds reported to date. Making any reliable prediction as to activities or oral absorptions of new cephalosporin compounds from an examination of the properties of structurally analogous prior art compounds has also been found to be essentially impossible. To illustrate the unpredictability of oral absorption and antibacterial activity in a closely related series of cephalosporin compounds, Tables 1–8 below compare in vitro activities and oral absorption as tested in the mouse of the compounds of the formula

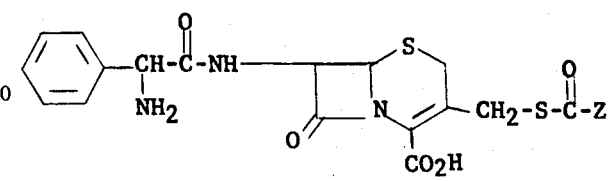

D-(-)

wherein

|   | Z = | Compound No. |
|---|---|---|
|   | 2-thiazolyl | 567 |
| = | 4-thiazolyl | 591 |
| = | 5-thiazolyl | 602 |
| = | 4-methyl-2-thiazolyl | 556 |
| = | 5-methyl-2-thiazolyl | 586 |
| = | 2-methyl-4-thiazolyl | 607 |
| = | 4,5-dimethyl-2-thiazolyl | 587 |

Tables 1–8 include data on the commercial oral cephalosporin, cephalexin.

Samples of the seven cephalosporin compounds having the compound numbers reported above after solution in DMSO (dimethyl sulfoxide) at 14 mgm./ml. followed by dilution with Nutrient Broth were found to exhibit the following Minimum Inhibitory Concentrations (M.I.C.) in mcg./ml. versus the indicated microorganisms as determined by overnight incubation at 37° C. by Tube Dilution. The in vitro activity of cephalexin was also tested.

Table I

| Organism | M.I.C. in mcg./ml. | | |
|---|---|---|---|
|  |  | Compound No. 586 | Cephalexin |
| D. pneumoniae + 5% serum* | A9585 | .16 | .6 |
| Str. pyogenes + 5% serum* | A9604 | .3 | .3 |
| S. aureus Smith** | A9537 | .3 | 1.3 |
| S. aureus Smith + 50% serum** | A9537 | >63 | 2.5 |
| S. aureus BX 1633-2 at $10^{-3}$ dilution | A9606 | .6 | 4 |
| S. aureus BX 1633-2 at $10^{-2}$ dilution | A9606 | 4 | 8 |
| S. aureus methicillin-resistant at $10^{-3}$ dilution | A15097 | 4 | 32 |
| S. aureus at $10^{-3}$ dilution | A9748 | 8 | 32 |
| S. aureus at $10^{-2}$ dilution | A9748 | 63 | 125 |
| Sal. enteritidis** | A9531 | .3 | 4 |
| E. coli Juhl** | A15119 | 2 | 8 |
| E. coli** | A9675 | 4 | 16 |
| K. pneumoniae** | A9977 | 4 | 8 |
| K. pneumoniae** | A15130 | 32 | 16 |
| Pr. mirabilis** | A9900 | 16 | 4 |
| Pr. morganii** | A15153 | 63 | >125 |
| Ps. aeruginosa** | A9843A | >125 | >125 |
| Ser. marcescens** | A20019 | >125 | >125 |

*50% Nutrient Broth - 45% Antibiotic Assay Broth
**at $10^{-4}$ dilution

Table II

| Organism | M.I.C. in mcg./ml. | | |
|---|---|---|---|
|  |  | Compound No. 567 | Cephalexin |
| D. pneumoniae + 5% serum* | A9585 | .04 | .6 |
| Str. pyogenes + 5% serum* | A9604 | .04 | .3 |
| S. aureus Smith** | A9537 | .3 | .6 |
| S. aureus Smith + 50% serum** | A9537 | 8 | 2.5 |
| S. aureus BX 1633-2 at $10^{-3}$ dilution | A9606 | .6 | 2 |
| S. aureus BX 1633-2 at $10^{-2}$ dilution | A9606 | 2 | 4 |
| S. aureus methicillin-resistant at $10^{-3}$ dilution | A15097 | 4 | 32 |
| S. aureus at $10^{-3}$ dilution | A9748 | 4 | 32 |
| S. aureus at $10^{-2}$ dilution | A9748 | 16 | 125 |
| Sal. enteritidis** | A9531 | .08 | 2 |
| E. coli Juhl** | A15119 | 1 | 8 |
| E. coli** | A9675 | 4 | 16 |

Table II-continued

| Organism | M.I.C. in mcg./ml. | | |
|---|---|---|---|
|  |  | Compound No. 567 | Cephalexin |
| K. pneumoniae** | A9977 | 2 | 4 |
| K. pneumoniae** | A15130 | 8 | 16 |
| Pr. mirabilis** | A9900 | 2 | 4 |
| Pr. morganii** | A15153 | 63 | >125 |
| Ps. aeruginosa** | A9843A | >125 | >125 |
| Ser. marcescens** | A20019 | 125 | >125 |

*50% Nutrient Broth - 45% Antibiotic Assay Broth
**at $10^{-4}$ dilution

Table III

| Organism | M.I.C. in mcg./ml. | | |
|---|---|---|---|
|  |  | Compound No. 591 | Cephalexin |
| D. pneumoniae + 5% serum* | A9585 | .02 | .3 |
| Str. pyogenes + 5% serum* | A9604 | .02 | .6 |
| S. aureus Smith** | A9537 | .3 | 1.3 |
| S. aureus Smith + 50% serum** | A9537 | 8 | 2.5 |
| S. aureus BX 1633-2 at $10^{-3}$ dilution | A9606 | .6 | 4 |
| S. aureus BX 1633-2 at $10^{-2}$ dilution | A9606 | 2 | 4 |
| S. aureus methicillin-resistant at $10^{-3}$ dilution | A15097 | 2 | 63 |
| S. aureus at $10^{-3}$ dilution | A9748 | 4 | 63 |
| S. aureus at $10^{-2}$ dilution | A9748 | 16 | 125 |
| Sal. enteritidis** | A9531 | .16 | 4 |
| E. coli Juhl** | A15119 | 1 | 8 |
| E. coli** | A9675 | 4 | 32 |
| K. pneumoniae** | A9977 | 1 | 4 |
| K. pneumoniae** | A15130 | 8 | 32 |
| Pr. mirabilis** | A9900 | 1 | 4 |
| Pr. morganii** | A15153 | 32 | >125 |
| Ps. aeruginosa** | A9843A | >125 | >125 |
| Ser. marcescens** | A20019 | 125 | >125 |

*50% Nutrient Broth - 45% Antibiotic Assay Broth
**at $10^{-4}$ dilution

Table IV

| Organism | M.I.C. in mcg./ml. | | |
|---|---|---|---|
|  |  | Compound No. 607 | Cephalexin |
| D. pneumoniae + 5% serum* | A9585 | .16 | .16 |
| Str. pyogenes + 5% serum* | A9604 | .16 | .16 |
| S. aureus Smith** | A9537 | .3 | .6 |
| S. aureus Smith + 50% serum** | A9537 | 63 | 1.3 |
| S. aureus BX 1633-2 at $10^{-3}$ dilution | A9606 | .6 | 2 |
| S. aureus BX 1633-2 at $10^{-2}$ dilution | A9606 | 4 | 8 |
| S. aureus methicillin-resistant at $10^{-3}$ dilution | A15097 | 8 | 63 |
| S. aureus at $10^{-3}$ dilution | A9748 | 8 | 63 |
| S. aureus at $10^{-2}$ dilution | A9748 | 16 | 125 |
| Sal. enteritidis** | A9531 | .6 | 4 |
| E. coli Juhl** | A15119 | 8 | 8 |
| E. coli** | A9675 | 16 | 16 |
| K. pneumoniae** | A9977 | 16 | 4 |
| K. pneumoniae** | A15130 | 125 | 16 |
| Pr. mirabilis** | A9900 | 8 | 8 |
| Pr. morganii** | A15153 | 32 | >125 |
| Ps. aeruginosa** | A9843A | >125 | >125 |
| Ser. marcescens** | A20019 | >125 | >125 |

*50% Nutrient Broth - 45% Antibiotic Assay Broth
**at $10^{-4}$ dilution

Table V

| Organism | M.I.C. in mcg./ml. | | |
|---|---|---|---|
| | | Compound No. 602 | Cephalexin |
| D. pneumoniae + 5% serum* | A9585 | .6 | .3 |
| Str. pyogenes + 5% serum* | A9604 | .6 | .6 |
| S. aureus Smith** | A9537 | .3 | 1.3 |
| S. aureus Smith + 50% serum** | A9537 | >63 | 2.5 |
| S. aureus BX 1633-2 at $10^{-3}$ dilution | A9606 | 1.3 | 4 |
| S. aureus BX 1633-2 at $10^{-2}$ dilution | A9606 | 16 | 8 |
| S. aureus methicillin-resistant at $10^{-3}$ dilution | A15097 | 4 | 32 |
| S. aureus at $10^{-3}$ dilution | A9748 | 8 | 32 |
| S. aureus at $10^{-2}$ dilution | A9748 | 63 | 63 |
| Sal. enteritidis** | A9531 | .3 | 4 |
| E. coli Juhl** | A15119 | 4 | 8 |
| E. coli** | A9675 | 16 | 32 |
| K. pneumoniae** | A9977 | 16 | 8 |
| K. pneumoniae** | A15130 | 32 | 16 |
| Pr. mirabilis** | A9900 | 16 | 8 |
| Pr. morganii** | A15153 | 125 | >125 |
| Ps. aeruginosa** | A9843A | >125 | >125 |
| Ser. marcescens** | A20019 | >125 | >125 |

*50% Nutrient Broth - 45% Antibiotic Assay Broth
**at $10^{-4}$ dilution

Table VI

| Organism | M.I.C. in mcg./ml. | | |
|---|---|---|---|
| | | Compound No. 587 | Cephalexin |
| D. pneumoniae + 5% serum* | A9585 | 2.5 | .3 |
| Str. pyogenes + 5% serum* | A9604 | 2.5 | 1.3 |
| S. aureus Smith** | A9537 | .3 | 1.3 |
| S. aureus Smith + 50% serum** | A9537 | >63 | 2.5 |
| S. aureus BX 1633-2 at $10^{-3}$ dilution | A9606 | .6 | 4 |
| S. aureus BX 1633-2 at $10^{-2}$ dilution | A9606 | 1 | 4 |
| S. aureus methicillin-resistant at $10^{-3}$ dilution | A15097 | 4 | 63 |
| S. aureus at $10^{-3}$ dilution | A9748 | 4 | 63 |
| S. aureus at $10^{-2}$ dilution | A9748 | 16 | 125 |
| Sal. enteritidis** | A9531 | 2.5 | 4 |
| E. coli Juhl** | A15119 | 16 | 8 |
| E. coli** | A9675 | 32 | 16 |
| K. pneumoniae** | A9977 | 32 | 4 |
| K. pneumoniae** | A15130 | >125 | 16 |
| Pr. mirabilis** | A9900 | >125 | 4 |
| Pr. morganii** | A15153 | >125 | >125 |
| Ps. aeruginosa** | A9843A | >125 | >125 |
| Ser. marcescens** | A20019 | >125 | >125 |

*50% Nutrient Broth - 45% Antibiotic Assay Broth
*at $10^{-4}$ dilution

Table VII

| Organism | M.I.C. in mcg./ml. | | |
|---|---|---|---|
| | | Compound No. 556 | Cephalexin |
| D. pneumoniae + 5% serum* | A9585 | 1.3 | .16 |
| Str. pyogenes + 5% serum* | A9604 | 2.5 | .08 |
| S. aureus Smith** | A9537 | 1.3 | .6 |
| S. aureus Smith + 50% serum** | A9537 | 63 | 1.3 |
| S. aureus BX 1633-2 at $10^{-3}$ dilution | A9606 | 1.3 | 2 |
| S. aureus BX 1633-2 at $10^{-2}$ dilution | A9606 | 4 | 4 |
| S. aureus methicillin-resistant at $10^{-3}$ dilution | A15097 | 4 | 32 |
| S. aureus at $10^{-3}$ dilution | A9748 | 4 | 32 |
| S. aureus at $10^{-2}$ dilution | A9748 | 8 | 63 |
| Sal. enteritidis** | A9531 | 1 | 2 |
| E. coli Juhl** | A15119 | 32 | 8 |
| E. coli** | A9675 | 32 | 16 |
| K. pneumoniae** | A9977 | 32 | 4 |
| K. pneumoniae** | A15130 | 125 | 16 |
| Pr. mirabilis** | A9900 | 32 | 4 |
| Pr. morganii** | A15153 | 125 | >125 |
| Ps. aeruginosa** | A9843A | 125 | >125 |
| Ser. marcescens** | A20019 | 63 | >125 |

*50% Nutrient Broth - 45% Antibiotic Assay Broth
**at $10^{-4}$ dilution

Table VIII

Blood levels in the mouse after oral administration were determined with the following results:

Structure: phenyl-CH(NH₂)-CONH- attached to cephalosporin nucleus with -CH$_2$R substituent and CO$_2$H group.

R =

| | Blood Level in mcg./ml. | | | |
|---|---|---|---|---|
| Dose mgm./kg. | 0.5 | 1 | 2 | 3.5 |
| | Hrs. after administration. | | | |
| 586: $-S-C(=O)-N=C(S-)-CH_3$ (thiadiazole) | | | | |
| 100 | 34.8 | 30.7 | 13.0 | 7.0 |
| 567: $-S-C(=O)-N=CH-S-$ (thiazole) | | | | |
| 100 | 16.0 | 14.1 | 3.4 | <0.4 |

Table VIII-continued

Blood levels in the mouse after oral administration were determined with the following results:

| Structure | | | | | |
|---|---|---|---|---|---|
| 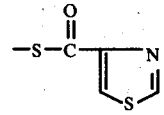 591 | 100 | 6.5 | 7.9 | 4.4 | 3.2 |
| 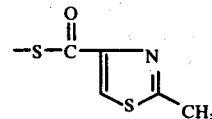 607 | 100 | 1.2 | 1.4 | 1.3 | 1.0 |
| 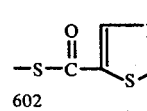 602 | 100 | 11.7 | 17.6 | 9.7 | 3.3 |
| 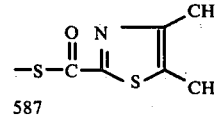 587 | 100 | 6.3 | 8.9 | 4.3 | 2.0 |
| 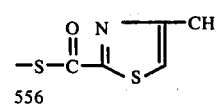 556 | 100 | 15.2 | 16.2 | 7.8 | <2.1 |
| —H (cephalexin) monohydrate | 100 | 44.6 | 23.4 | 6.1 | 1.7 |

An examination of Table VIII shows that very small structural changes in the 3-acylthiomethyl substituent can greatly affect oral absorption. The very closely-related compounds 586, 607 and 556, for example, have blood levels after 30 minutes of 34.8, 1.2 and 15.2 mcg./ml. An examination of Table I – VII shows the same unpredictability with respect to in vitro activities. Compounds 586 and 567 claimed in the present invention surprisingly and unexpectedly showed both excellent activity relative to cephalexin in the primary screening tests and good oral absorption properties.

The novel medicaments provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or dragees, or in liquid form such as solutions, suspensions or emulsions. In the treatment of bacterial infections in man, the compounds of this invention may be administered in an amount of from about 5 to 200 mg./kg./day in divided dosage, e.g. 3 to 4 times a day. They are administered in dosage units containing e.g. 125, 250 or 500 mg. of active ingredient with suitable physiologically acceptable carriers or excipients.

In the experimental sections which follow, all temperatures unless indicated are in degrees Centigrade. The abbreviation "MeCl₂" is used to refer to methylene chloride while "TEA" is used to indicate triethylamine.

PREPARATION OF STARTING MATERIALS

Thiazole-2-thiocarboxylic acid dicyclohexylamine salt

A mixture of 14.2 g. (0.11 moles) of 2-carboxy-thiazole, 220 ml. of methylene chloride, 13.9 g. (0.11 moles) of oxalyl chloride and 0.5 ml. of N,N-dimethylformamide was stirred for 3 hours. The insoluble material was removed by filtration, washed with methylene chloride and the filtrate was evaporated under reduced pressure to a solid. This obtained acid chloride was added portionwise to a stirred and cooled solution of 24.2 g. (0.22 moles) of sodium sulfhydrate trihydrate in 247.5 ml. of ethanol and 27.5 ml. of water at such a rate as to maintain the temperature of the reaction mixture at 10–15°. After the addition was completed, the mixture was stirred for 40 minutes at 5°–10°. Then the ethanol was removed under reduced pressure and the residue was dissolved in 145 ml. of water. The pH of the solution was lowered to 2.8 by the addition of 6 N hydrochloric acid, and maintained there while the mixture was extracted with 5 × 200 ml. of ethyl acetate. The combined extracts were washed with ice water, dried over MgSO₄, filtered and evaporated under reduced pressure to a reddish solid. This was weighed, redissolved in 100 ml. of warm ethyl acetate and 1 equivalent of dicyclohexylamine was added. Bright yellow crystals started to precipitate immediately. The mixture was cooled in an ice-bath for 1 hour. Then the crystals were removed by filtration, washed with ether and dried under reduced pressure for 15 hours; weight 15.2 g. (42.5% yield).

Analysis: Calcd. for $C_{16}H_{26}N_2OS_2$: C, 58.88; H, 8.04; N, 8.62; S, 19.60. Found: C, 58.47; H, 8.11; N, 8.74; S, 19.91.

7-Amino-3-(2-thiazolyl)carbonylthiomethyl-3-cephem 4-carboxylic acid

Fifteen g. of thiazole-2-thiocarboxylic acid dicyclohexylamine salt was slurried in 175 ml. of water and layered with 175 ml. of ethyl acetate. The pH of the cooled solution was lowered to 2.2 by the addition of 6 N hydrochloric acid. The layers were separated and the aqueous phase was extracted with 2 × 175 ml. of ethyl acetate. The combined extracts were dried over $MgSO_4$, filtered and concentrated to a red solid, weight 5.35 g. The infrared spectrum indicated thioacid.

To a stirred solution of 9.8 g. (0.036 moles) of 7-aminocephalosporanic acid and 6.05 g. (0.072 moles) of sodium bicarbonate in 170 ml. of aqueous phosphate buffer at pH 6.4 was added 5.35 g. (0.036 moles) of thiazole-2-thiocarboxylic acid. The mixture was stirred in a nitrogen atmosphere at 50° for 5 hours keeping the pH at 6.6 with 42% phosphoric acid. Then the mixture was cooled to 20° and the precipitated solid was removed by filtration, washed with water, acetone and ether and dried in vacuo over phosphorus pentoxide to provide 4.6 g. (35% yield) of a tan crystalline solid. Infrared and NMR spectra were consistent with the structure.

Pivaloyloxymethyl 7-amino-3-(2-thiazolyl)carbonylthiomethyl-3-cephem-4-carboxylate Method A The title compound is produced by substituting for the 7-aminocephalosporanic acid used immediately above an equimolar weight of pivaloyloxymethyl 7-aminocephalosporanate hydrochloride prepared according to Example 2 of U.K. Pat. No. 1,229,453 from 7-aminocephalosporanic acid. German Pat. No. 1,904,585 (Farmdoc 39,445) is equivalent to U.K. Pat. No. 1,339,453.

Method B

The title compound is produced by substituting for the 0.025 mole (6.8 g.) 7-aminocephalosporanic acid used in the procedure of Example 2 of U.K. Pat. No. 1,229,453 an equimolar weight of 7-amino-3-(2-thiazolyl)carbonylthiomethyl-3-cephem-4-carboxylic acid.

The respective acetoxymethyl, methoxymethyl, acetonyl and phenacyl esters of 7-amino-3-(2-thiazolyl)carbonylthiomethyl-3-cephem4-carboxylic acid are prepared by substituting in Method B above for the chloromethyl pivalate used therein an equimolar weight of chloromethyl acetate, chloromethyl methyl ether, chloroacetone and phenacyl bromide, respectively.

5-Methylthiazole-2-thiocarboxylic acid dicyclohexylamine salt

A mixture of 14.3 g. (0.1 mole) of 5-methylthiazole-2-carboxylic acid in 200 ml. of dry methylene chloride, 12.6 g. (0.1 mole) of oxalyl chloride and 0.5 ml. of N,N-dimethylformamide was stirred for 3 hours at room temperature until a clear solution resulted. It was concentrated to a greenish oil, which was identified by infrared as the acid chloride. This was added slowly over 5 minutes to a stirred and cooled solution of 22.0 g. (0.2 moles) of sodium sulfhydrate trihydrate in 225 ml. of 100% ethanol and 25 ml. of water at such a rate as to keep the temperature of the mixture at 10°–15° C. After the addition was completed, the reaction mixture was stirred for 40 minutes at 5°–10°. Then most of the ethanol was removed under reduced pressure and the residue was dissolved in 130 ml. of water. The pH of the solution was lowered to 2.8 with 6 N hydrochloric acid and was maintained there, while the mixture was extracted with 5 × 200 ml. of ethyl acetate. The combined extracts were washed with ice water, dried over anhydrous magnesium sulfate, filtered and concentrated under reduced pressure to an orange solid. This was weighed, redissolved in 100 ml. of warm ethyl acetate and 1 equivalent (8.25 ml., 0.067 moles) of dicyclohexylamine was added. Bright yellow crystals started to precipitate immediately. The mixture ws cooled for 2 hours in an ice bath. Then the crystals were removed by filtration, washed with ether, and dried in vacuo yielding 14 g. (41% yield). IR and NMR spectra were consistent with structure.

Analysis: Calcd. for $C_{17}H_{28}N_2OS_2.1/2$ $H_2O$: C, 58.41; H, 8.36 N, 8.02; S, 18.35. Found: C, 58.78; H, 8.22; N, 8.11; S, 19.30.

7Amino-3-(5-methylthiazol-2-yl)carbonylthiomethyl-3-cephem-4-carboxylic acid 5-methylthiazole-2-thiocarboxylic acid dicyclohexylamine salt (13.5 g.) was slurried in 150 ml. of water and layered with 150 ml. of ethyl acetate. The pH of the cooled solution was lowered to 2.2 with 6N hydrochloric acid. The layers were separated and the aqueous phase was extracted with 3 × 100 ml. of ethyl acetate. The combined extracts were dried over anhydrous magnesium sulfate, filtered and concentrated to a red solid which was identified by infrared as thioacid; weight 5.44 g.

To a stirred solution of 9.3 g. (0.034 moles) of 7-aminocephalosporanic acid and 5.75 g. (0.068 moles) of sodium bicarbonate in 204 ml. of aqueous phosphate buffer at pH 6.4 was added 5.44 g. (0.034 moles) of 5-methylthiazole-2-thiocarboxylic acid. The mixture was stirred in a nitrogen atmosphere at 50° for 5 hours keeping the pH at 6.5 with 42% phosphoric acid. Then the mixture was cooled to 20° and the precipitated solid was removed by filtration, washed with water, acetone and ether and dried in vacuo over phosphorus pentoxide to provide 4.4 g. (35% yield) of a tan crystalline solid. Infrared and NMR spectra were consistent with the structure.

Pivaloyloxymethyl 7-amino-3-(5-methylthiazol-2-yl)carbonylthiomethyl-3-cephem-4-carboxylate Method A The title compound is produced by substituting for the 7-aminocephalosporanic acid used immediately above an equimolar weight of pivaloyloxymethyl 7-aminocephalosporanate hydrochloride prepared according to Example 2 of U.K. Pat. No. 1,229,453 from 7-aminocephalosporanic acid. German Pat. No. 1,904,585 (Farmdoc 39,445) is equivalent to U.K. Pat. No. 1,339,453.

Method B

The title compound is produced by substituting for the 0.025 mole (6.8 g.) 7-aminocephalosporanic acid used in the procedure of Example 2 of U.K. Pat. No. 1,229,453 an equimolar weight of 7-amino-3-(5- methylthiazol-2-yl)carbonylthiomethyl-3-cephem-4-carboxylic acid.

The respective acetoxymethyl, methoxymethyl, acetonyl and phenacyl esters of 7-amino-3-(5-methyl-thiazol-2yl)carbonylthiomethyl-3-cephem-4-carboxylic acid are prepared by substituting in Method B above for the chloromethyl pivalate used therein an equimolar weight of chloromethyl acetate, chlorometyl methyl ether, chloroacetone and phenacyl bromide, respectively.

EXAMPLES

The following examples are given in illustration of, but not in limitation of, the present invention.

EXAMPLE 1

7-[D-(−)-α-Aminophenylacetamido]-3-(thiazol-2-yl)carbonylthiomethyl-3-cephem-4-carboxylic acid

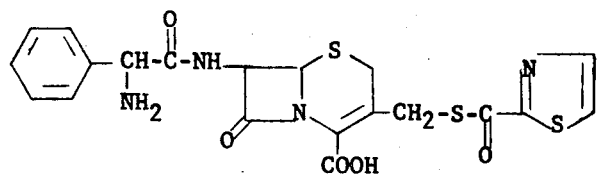

(BL-S567)

To a stirred slurry of 4.5 g. (0.0126 moles) of 7-amino-3-(thiazol-2-yl)carbonylthiomethyl-3-cephem-4-carboxylic acid in 125 ml. of dry methylene chloride were added successively 3.52 ml. (0.0252 moles) of triethylamine, 1.62 ml. (0.0126 moles) of N,N-dimethylaniline and 4.72 ml. (0.0378 moles) of trimethylchlorosilene. After being refluxed for 0.5 hour a clear brown solution resulted. It was cooled to 0°–5° and 2.86 g. (0.0138 moles) of D-(−)-2-phenylglycyl chloride hydrochloride was added. The resulting slurry was stirred for 2 hours letting the temperature rise to 25°. This was then added to 125 ml. of ice water. The resulting tan precipitate was stirred for 15 minutes at room temperature, filtered, washed with water, acetone and ether and dried in vacuo over phosphorus pentoxide yielding 3.8 g. of a tan solid. The layers of the filtrate were separated and the aqueous phase was cooled, layered with 100 ml. of ethyl acetate and adjusted with 10% sodium hydroxide to pH 4.2. The resulting white solid was removed by filtration, washed with water, acetone and ether and dried in vacuo over phosphorous pentoxide to give 475 mg. The 3.8 g. of the first precipitated solid was purified by slurrying in 50 ml. of water and 50 ml. of ethyl acetate and acidifying to pH 1.5 with 6 N hydrochloric acid. It was stirred for 15 minutes and then filtered. The filtrate was treated with 10% sodium hydroxide to give pH 4.5. The solid which precipitated was collected by filtration, washed with water, acetone and ether and dried in vacuo over phosphorus pentoxide to give another 900 mg. Combined solids weighed 1.37 g. (22%). Infrared and NMR spectra were consistent with structure of the title product.

Analysis: Calcd. for: $C_{20}H_{18}N_4O_5S_3 \cdot H_2O$: C, 47.60; H, 3.98; N, 11.03. Found: C, 47.40; H, 3.89; N, 10.79.

EXAMPLE 2

Sodium 7-[D-(−)-α-aminophenylacetamido]-3-(thiazol2-yl)carbonylthiomethyl-3-cephem-4-carboxylate

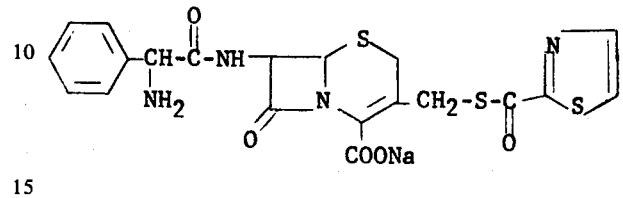

To a stirred aqueous suspension of the zwitterionic form of 7-[D-(−)-α-aminophenylacetamido]-3-(thiazol-2-yl)carbonylthiomethyl-3-cephem-4-carboxylic acid (0.8 mmole) is added 1N aqueous NaOH at room temperature until a clear solution (pH 10.8) is obtained. The solution is immediately freeze-dried to give impure, solid sodium 7-[D-(−)-α-aminophenylacetamido)]-3-(thiazol-2-yl)carbonylthiomethyl-3-cephem-4-carboxylate.

Following the same general procedure as above, use of 1N KOH in place of the 1N NaOH used therein produces potassium 7-[D-(−)-α-aminophenylacetamido]-3-(thiazol-2-yl)carbonylthiomethyl-3-cephem-4carboxylate.

EXAMPLE 3

7-[D-α-amino-α-(3-thianyl)acetamido]-3-(thiazol-2-yl)carbonylthiomethyl-3-cephem-4-carboxylic acid

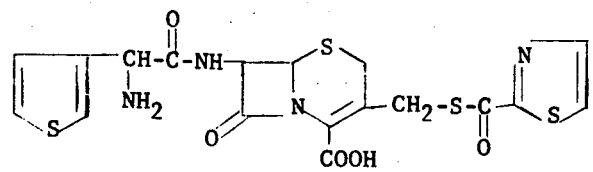

The above compound is prepared by substituting an equimolar weight of D-(−)-α-amino-α-(3-thienyl) acetyl chloride hydrochloride in the procedure of Example 1 for the D-(−)-α-amino-α-phenylacetyl chloride hydrochloride used therein.

EXAMPLE 4

7-[D-α-amino-α-(2-thienyl)acetamido]-3-(thiazol-2-yl)carbonylthiomethyl-3-cephem-4-carboxylic acid

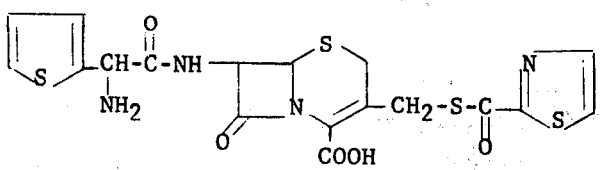

The above compound is prepared by substituting an equimolar weight of D-(—)-α-amino-α-(2-thienyl) acetyl chloride hydrochloride in the procedure of Example 1 for the D-(—)-60 -amino-α-phenylacetyl chloride hydrochloride used therein.

EXAMPLE 5

Acetoxymethyl 7-[D-(—)-α-aminophenylacetamido]-3-(thiazol-2-yl)carbonylthiomethyl-3-cephem-4-carboxylate

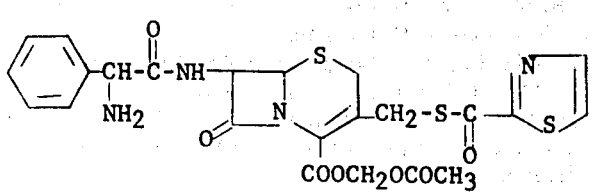

To a solution of acetoxymethyl 7-amino-3-(2-thiazolyl)carbonylthiomethyl-3-cephem-4-carboxylate (regenerated from 0.009 mole of its hydrochloride) in 30 ml. ethyl acetate is added 0.020 mole pyridine. The mixture is cooled in ice and stirred while 0.010 mole D-(—)-2-phenylglycyl chloride hydrochloride in 30 ml. ethyl acetate is added over 10 minutes. After a further 20 minutes in the cold, stirring is continued at room temperature for 1 hour. Then the mixture is washed successively with aqueous $NaHCO_3$, 0.1 N HCl and water, dried and evaporated in vacuo to leave the desired acetoxymethyl 7-[D-(—)-α-aminophenylacetamido]-3-(thiazol-2-yl)carbonylthiomethyl-3-cephem-4-carboxylate as an oil which crystallizes upon trituration in cyclohexane.

The respective pivaloyloxymethyl, methoxymethyl, acetonyl and phenacyl esters corresponding to the above acetoxymethyl ester are produced by replacing the acetoxymethyl 7-amino-3-(2-thiazolyl)-carbonyl-thiomethyl-3-cephem-4-carboxylate hydrochloride used in the above procedure with 0.009 mole of the hydrochloride of pivaloyloxymethyl, methoxymethyl, acetonyl and phenacyl esters of 7-amino-3-(2-thiazolyl)carbonylthiomethyl-3-cephem-4-carboxylic acid, respectively.

EXAMPLE 6

Acetoxymethyl 7-[D-α-amino-α-(3-thienyl)acetamido]-3-(thiazol-2-yl)carbonylthiomethyl-3-cephem-4-carboxylate

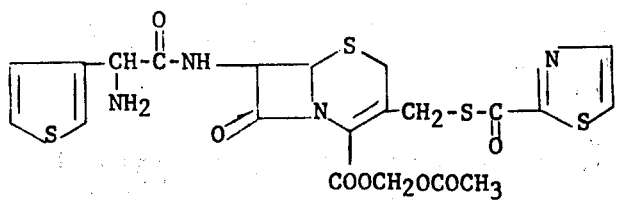

The above compound is prepared according to Example 5 by substituting for the D-(—)-2-phenylglycyl chloride hydrochloride used therein an equimolar amount of D-(—)-α-amino-α-(3-thienyl) acetyl chloride hydrochloride.

The respective pivaloyloxymethyl, methoxymethyl, acetonyl and phenacyl esters corresponding to the above acetoxymethyl ester are produced by replacing the acetoxymethyl 7-amino-3-(2-thiazolyl)-carbonyl-thiomethyl-3-cephem-4-carboxylate hydrochloride used in the above procedure with 0.009 mole of the hydrochloride of pivaloyloxymethyl, methoxymethyl, acetonyl and phenacyl esters of 7-amino-3-(2-thiazolyl)carbonylthiomethyl-3-cephem-4-carboxylic acid, respectively.

EXAMPLE 7

Acetoxymethyl 7-[D-α-amino-α-(2-thienyl)acetamido]-3-(thiazol-2-yl)carbonylthiomethyl-3-cephem-4-carboxylate

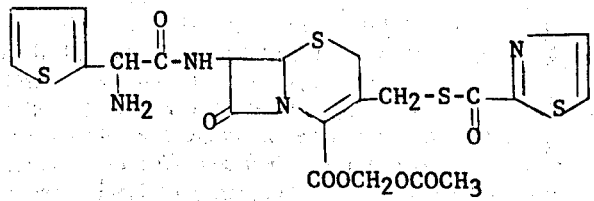

The above compound is prepared according to Example 5 by substituting for the D-(—)-2-phenylglycyl chloride hydrochloride used therein an equimolar amount of D-(—)-α-amino-α-(2-thienyl) acetyl chloride hydrochloride.

The respective pivaloyloxymethyl, methoxymethyl, acetonyl and phenacyl esters corresponding to the above acetoxymethyl ester are produced by replacing the acetoxymethyl 7-amino-3-(2-thiazolyl)-carbonylthiomethyl-3-cephem-4-carboxylate hydrochloride used in the above procedure with 0.009 mole of the hydrochloride of pivaloyloxymethyl, methoxymethyl, acetonyl and phenacyl esters of 7-amino-3-(2-thiazolyl)carbonylthiomethyl-3-cephem-4-carboxylic acid, respectively.

EXAMPLE 8

7-[D-(—)-α-Aminophenylacetamido]-3-(5-methylthiazol-2-yl)carbonylthiomethyl-3-cephem-4-carboxylic acid

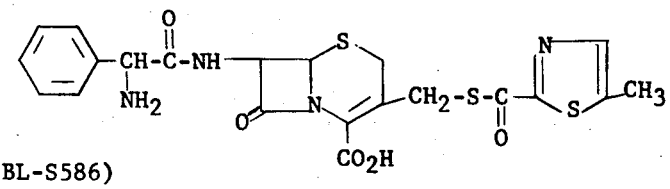

(BL-S586)

To a stirred slurry of 4.4 g. (0.0119 moles) of 7-amino-3-(5-methylthiazol-2-yl)carbonylthiomethyl-3-cephem-4-carboxylic acid in 120 ml. of dry methylene chloride were added successively 3.34 ml. (0.023 moles) of triethylamine, 1.51 ml. (0.0119 moles) of N,N-dimethylaniline and 4.45 ml. (0.0357 moles) of trimethylchlorosilane. After being refluxed for 40 minutes, a clear yellow solution resulted. It was cooled to 3° C. and 2.7 g. (0.0119 moles) of D-(—)-2-phenylglycyl chloride hydrochloride was added with vigorous stirring. The resulting slurry was stirred for 2 hours letting the temperature rise to 20°. This was then added to 120 ml. of ice water and the resulting tan precipitate was stirred for 30 minutes at room temperature. It was filtered, washed with water, acetone, and ether and dried in vacuo over phosphorus pentoxide yielding 4.1 g. of a tan solid. The layers of the filtrate of the tan solid were separated and the aqueous phase was cooled, layered with 100 ml. of ethyl acetate and adjusted with 10% sodium hydroxide to pH 4.2. The resulting white solid was removed by filtration, washed with water, acetone, and ether and dried in vacuo to give 75 mg.

The 4.1 g. of the first precipitated solid was purified by slurrying in 50 ml. of water and 50 ml. of ethyl acetate and acidifying to pH 1.5 with 6 N hydrochloric acid. It was stirred for 15 minutes and the insoluble material was filtered off. The filtrate was treated with 10% sodium hydroxide to give pH 4.5. The solid which precipitated was collected by filtration, washed with water, acetone, and ether and dried in vacuo over phosphorus pentoxide to give 575 mg. Combined solids weighed 650 mg. (11% yield). Infrared and NMR spectra were consistent with structure.

Analysis: Calcd. for $C_{21}H_{20}N_4O_5S_3 \cdot 2H_2O$: C, 46.65, H, 4.47; N, 10.35. Found: C, 47.06; H, 4.97; N, 9.35.

EXAMPLE 9

Sodium 7-[D-(—)-α-aminophenylacetamido]-3-(5-methylthiazol-2-yl)carbonylthiomethyl-3-cephem-4-carboxylate

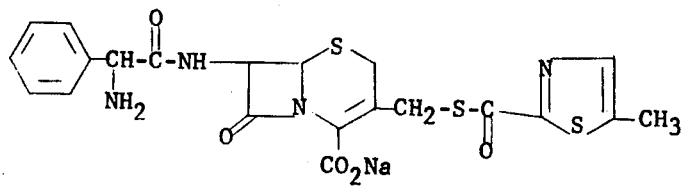

To a stirred aqueous suspension of the zwitterionic form of 7-[D-(—)-α-aminophenylacetamido]-3-(5-methylthiazol-2-yl)carbonylthiomethyl-3-cephem-4-carboxylic acid (0.08 mmole) is added 1N aqueous NaOH at room temperature until a clear solution (pH 10.8) is obtained. The solution is immediately freeze-dried to give impure, solid sodium 7-[D-(—)-α-aminophenylacetamido]-3-(5-methylthiazol-2-yl)carbonylthiomethyl-3-cephem-4-carboxylate.

Following the same general procedure as above, use of 1N KOH in place of the 1N NaOH used therein produces potassium 7-[D-(—)-α-aminophenylacetamido]-3-(5-methylthiazol-2-yl)carbonylthiomethyl-3-cephem-4-carboxylate.

EXAMPLE 10

7-[D-α-amino-α-(3-thienyl)acetamido]-3-(5-methylthiazol-2-yl)carbonylthiomethyl-3-cephem-4-carboxylic acid

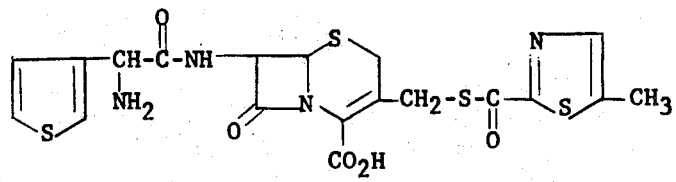

The above compound is prepared by substituting an equimolar weight of D-(—)-α-amino-α-(3-thienyl)- acetyl chloride hydrochloride in the procedure of Example 8 for the D-(—)-2-phenylglycyl chloride hydrochloride used therein.

EXAMPLE 11

7-[D-α-amino-α-(2-thienyl)acetamido]-3-(5-methylthiazol-2-yl)carbonylthiomethyl-3-cephem-4-carboxylic acid

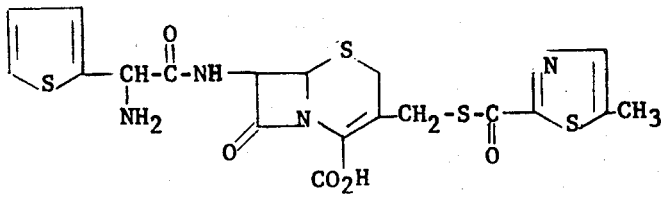

The above compound is prepared by substituting an equimolar weight of D-(—)-α-amino-α-(2-thienyl)-acetyl chloride hydrochloride in the procedure of Example 8 for the D-(—)-α-amino-2-phenylglycyl chloride hydrochloride used therein.

EXAMPLE 12

Acetoxymethyl 7-[D-(—)-α-aminophenylacetamido]-3-(5-methylthiazol-2-yl)carbonylthiomethyl-3-cephem-4-carboxylate.

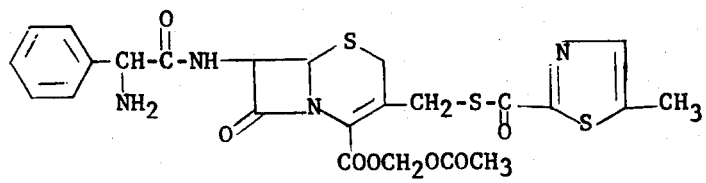

To a solution of acetoxymethyl 7-amino-3-(5-methylthiazol-2-yl)carbonylthiomethyl-3-cephem-4-carboxylate (regenerated from 0.009 mole of its hydrochloride) in 30 ml. ethyl acetate is added 0.020 mole pyridine. The mixture is cooled in ice and stirred while 0.010 mole D-(—)-2-phenylglycyl chloride hydrochloride in 30 ml. ethyl acetate is added over 10 minutes. After a further 20 minutes in the cold, stirring is continued at room temperature for 1 hour. Then the mixture is washed successively with aqueous NaHCO₃, 0.1 N HCl and water, dried and evaporated in vacuo to leave the desired acetoxymethyl 7-[D-(—)-α-aminophenylacetamido]-3-(5-methylthiazol-2-yl)carbonylthiomethyl-3-cephem-4-carboxylate as an oil which crystallizes upon trituration in cyclohexane.

The respective pivaloyloxymethyl, methoxymethyl, acetonyl and phenacyl esters corresponding to the above acetoxymethyl ester are produced by replacing the acetoxymethyl 7-amino-3-(5-methylthiazol-2-yl)-carbonylthiomethyl-3-cephem-4-carboxylate hydrochloride used in the above procedure with 0.009 mole of the hydrochloride of pivaloyloxymethyl, methoxymethyl, acetonyl and phenacyl esters of 7-amino-3-(5-methylthiazol-2-yl)carbonylthiomethyl-3-cephem-4-carboxylic acid respectively.

EXAMPLE 13

Acetoxymethyl 7-[D-α-amino-α-(3-thienyl)acetamido]-3-(5-methylthiazol-2-yl)carbonylthiomethyl-3-cephem-4-carboxylate

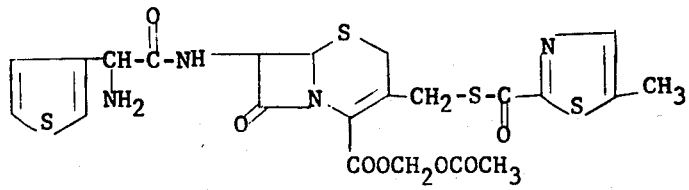

The above compound is prepared according to Example 12 by substituting for the D-(—)-2-phenylglycyl chloride hydrochloride used therein an equimolar amount of D-(—)-α-amino-α-(3-thienyl)-acetyl chloride hydrochloride.

The respective pivaloyloxymethyl, methoxymethyl, acetonyl and phenacyl esters corresponding to the above acetoxymethyl ester are produced by replacing the acetoxymethyl 7-amino-3-(5-methylthiazol-2-yl)carbonylthiomethyl-3-cephem-4-carboxylate hydrochloride used in the above procedure with 0.009 mole of the hydrochloride of pivaloyloxymethyl, methoxymethyl, acetonyl and phenacyl esters of 7-amino-3-(5-methylthiazol-2-yl)carbonylthiomethyl-3-cephem-4-carboxylic acid, respectively.

EXAMPLE 14

Acetoxymethyl 7-[D-α-amino-α-(2-thienyl)acetamido]-3-(5-methylthiazol-2-yl)carbonylthiomethyl-3-cephem-4-carboxylate

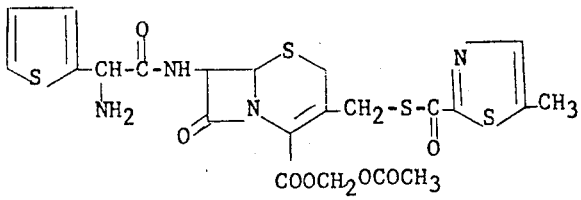

COOCH$_2$OCOCH$_3$

The above compound is prepared according to Example 12 by substituting for the D-(−)-2-phenylglycyl chloride hydrochloride used therein an equimolar amount of D-(−)-α-amino-α-(2-thienyl)-acetyl chloride hydrochloride.

The respective pivaloyloxymethyl, methoxymethyl, acetonyl and phenacyl esters corresponding to the above acetoxymethyl ester are prepared by replacing the acetoxymethyl 7-amino-3-(5-methylthiazol-2-yl)carbonylthiomethyl-3-cephem-4-carboxylate hydrochloride used in the above procedure with 0.009 mole of the hydrochloride of pivaloyloxymethyl, methoxymethyl, acetonyl and phenacyl esters of 7-amino-3-(5-methylthiazol-2-yl)carbonylthiomethyl-3-cephem-4-carboxylic acid, respectively.

EXAMPLE 15

The general procedure of Example 2 is repeated using the zwitterionic forms of the acids shown below in place of the 7-[D-(−)-α-aminophenylacetamido]-3-(thiazol-2-yl)carbonylthiomethyl-3-cephem-4-carboxylic acid used therein.
Use of:

7-[D-α-amino-α-(3-thienyl)acetamido]-3-(thiazol-2-yl)carbonylthiomethyl-3-cephem-4-carboxylic acid, 7-[D-α-amino-α-(2-thienyl)acetamido]-3-(thiazol-2-yl)carbonylthiomethyl-3-cephem-4-carboxylic acid, 7-[D-α-amino-α-(3-thienyl)acetamido]-3-(5-methylthiazol-2-yl)carbonylthiomethyl-3-cephem-4-carboxylic acid, and 7-[D-α-amino-α-(2-thienyl)acetamido]-3-(5-methylthiazol-2-yl)carbonylthiomethyl-3-cephem-4-carboxylic acid produced, respectively, sodium 7-[D-α-amino-α-(3-thienyl)acetamido]-3-(thiazol-2-yl)carbonylthiomethyl-3-cephem-4-carboxylate, potassium 7-[D-α-amino-α-(3-thienyl)acetamido]-3-(thiazol-2-yl)carbonylthiomethyl-3-cephem-4-carboxylate, sodium 7-[D-α-amino-α-(2-thienyl)acetamido]-3-(thiazol-2-yl)carbonylthiomethyl-3-cephem-4-carboxylate, potassium 7-[D-α-amino-α-(2-thienyl)acetamido]-3-(thiazol-2-yl)carbonylthiomethyl-3-cephem-4-carboxylate, sodium 7-[D-α-amino-α-(3-thienyl)acetamido]-3-(5-methylthiazol-2-yl)carbonylthiomethyl-3-cephem-4-carboxylate, potassium 7-[D-α-amino-α-(3-thienyl)acetamido]-3-(5-methylthiazol-2-yl)carbonylthiomethyl-3-cephem-4-carboxylate, sodium 7-[D-α-amino-α-(2-thienyl)acetamido]-3-(5-methylthiazol-2-yl)carbonylthiomethyl-3-cephem-4-carboxylate, and potassium 7-[D-α-amino-α-(2-thienyl)acetamido]-3-(5-methylthiazol-2-yl)carbonylthiomethyl-3-cephem-4-carboxylate.

PREPARATION OF COMPARATIVE COMPOUNDS

A. Thiazole-4-thiocarboxylic acid potassium salt

A solution of potassium hydrogen sulfide in ethanol was prepared by dissolving potassium metal (11.7 g., 0.300 moles) in 380 ml. of absolute ethanol under an atmosphere of dry nitrogen, cooling to 5° C., and saturating the solution with hydrogen sulfide. Thiazole-4-carbonyl chloride (22.0 g., 0.149 moles) [H. Erlenmeyer and Ch. J. Morel. Helv. Chim. Acta 28, 362(1945)] was suspended in 200 ml. of dry benzene and added portionwise at 5° C. under an atmosphere of dry nitrogen to the freshly prepared potassium hydrogen sulfide solution. When the addition was complete, the mixture was allowed to come to room temperature and stirred for 2 hours. The mixture was then evaporated under reduced pressure and the residue slurried with ether and collected by filtration.

This material was extracted with 900 ml. of boiling ethanol and filtered to remove the insoluble potassium chloride. Ether was added to turbidity and it was left to cool. The solid thiazole-4-thiocarboxylic acid potassium salt was collected by filtration and dried. The yield was 24.6 g (90%) with m.p. 206° – 209° C.

A sample crystallized several times from ethanol had m.p. 212°–213° C.

Calcu. for: C$_4$H$_2$KNOS$_2$: C, 26.21; H, 1.10; N, 7.64. Found: C, 26.32; H, 1.24; N, 7.86.

7-amino-3-(thiazol-4-yl)carbonylthiomethyl-3-cephem-4-carboxylic acid

A solution of 68% potassium thiazole-4-thiocarboxylate (5.4 g., 0.02 mole) in 100 ml. water was washed with 100 ml. of ether and then 200 ml. of pH 6.4 phosphate buffer and 7-aminocephalosporanic acid (5.5 g., 0.02 mole) was added. The mixture was heated at 48° for 4 hours as the pH was kept at 6.4 with NaHCO$_3$ solution. The solution was then cooled and acidified with 40% H$_3$PO$_4$ to pH 5.2. The product was collected by filtration, washed with water and acetone, and air dried overnight to yield 3.0 g. The material was not further purified and IR and NMR spectra were consistent with required structure.

7-[D-(-)α-aminophenylacetamido]-3-(thiazol-4-yl)carbonylthiomethyl-3-cephem-4-carboxylic acid

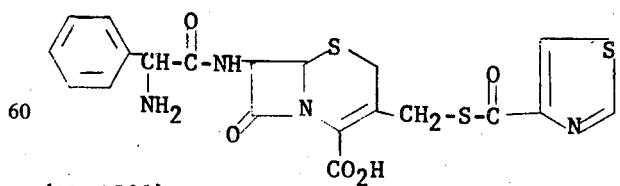

(BL-S591)

To a stirred suspension of 7-amino-3-(thiazol-4-yl)carbonylthiomethyl-3-cephem-4-carboxylic acid (2.44 g., 0.006 mole) in 50 ml. of MeCl$_2$ was added TEA (1.6 ml., 0.011 mole), N,N-dimethylaniline (0.9 ml., 0.007 mole) and with cooling to 5°, trimethylchlorosilane (1.5 ml., 0.012 mole). After stirring 1 hour at 25°, the mixture was refluxed for 30 minutes, cooled to 5° and 50% N,N-dimethylaniline . HCl in $MeCl_2$ (0.5 ml.), and D-(-)-2-phenylglycyl chloride hydrochloride (1.3 g., 0.006 mole) were added. The mixture was stirred for 1.5 hours at 3° and 1 hour at room temperature and then 50 ml. of water was added. After 15 minutes stirring, the pH was adjusted to 2.5 with 10% NaOH and the mixture was filtered. The solid collected was washed with water and acetone and then air dried to give 2.7 g. of crude product. This was recrystallized by stirring 1.7 g. in 50 ml. $H_2O$ and 50 ml. ethyl acetate and then acidifying to pH 1.5 with 6N HCl. Some insoluble material was then filtered, the filtrate layers were separated, and the aqueous phase was adjusted to pH 4.5 with solid $Na_2CO_3$. The product obtained was washed with water and dried in vacuum dessicator (15 mm, $P_2O_5$, room temperature) to give a yield of 500 mg. The IR and NMR spectra were consistent with the title structure. The compound was found to have a decomposition point of 180° C.

Analysis: Calcd. for: $C_{20}H_{18}N_4O_5S_3 \cdot H_2O$: C, 47.2; H, 3.96; N, 11.0. Found: C, 46.6; H, 3.91; N, 10.66.

B. Thiazole-5-thiocarboxylic acid potassium salt

A solution of potassium hydrogen sulfide in ethanol was prepared by dissolving potassium metal (10.3 g, 0.262 moles) in 350 ml. of absolute ethanol under an atmosphere of dry nitrogen, cooling to 5° C., and saturating the solution with hydrogen sulfide. Thiazole-5-carbonyl chloride (19.4 g., 0.131 moles) [Soc. pour l'ind. chim. à Bâle. Ger. 668, 874, Dec. 12, 1938] was suspended in 180 ml. of dry benzene and added portionwise at 5° C. under an atmosphere of dry nitrogen to the potassium hydrogen sulfide solution. When the addition was complete, the mixture was allowed to come to room temperature and stirred for 2 hours. The mixture was then evaporated under reduced pressure and the residue slurried with ether and collected by filtration.

This material was extracted with 900 ml. of boiling ethanol and filtered to remove the insoluble potassium chloride. The ethanol solution was reduced to about one-half volume, treated with ether, and cooled. The solid thiazole-5-thiocarboxylic acid potassium salt was collected by filtration and dried. The yield was 20.0 g. (83%) with m.p. 198°–202° C.

A sample crystallized several times from ethanol had m.p. 211°–212° C. 7.64.

Analysis: Calcd. for: $C_4H_2KNOS_2$: C, 26.21; H, 1.10; N, 7.64. Found: C, 26.40; H, 1.23; N, 7.57.

7-amino-3-(5-thiazolyl)carbonylthiomethyl-3-cephem-4-carboxylic acid

To a stirred solution of 8.95 g. (0.0328 moles) of 7-aminocephalosporanic acid and 2.76 g. (0.0328 moles) of sodium bicarbonate in 150 ml. of aqueous phosphate buffer at pH 6.4 was added 6.0 g. (0.0328 moles) of thiazole-5-thiocarboxylic acid potassium salt. The mixture was stirred in a nitrogen atmosphere at 50° for 5 hours keeping the pH at 6.6 with 42% phosphoric acid. The mixture was cooled to 20° and the precipitated solid was removed by filtration, washed with water, acetone and ether and dried in vacuo over phosphorus pentoxide to provide 4.25 g. (36%) of a tan crystalline solid. Infrared and NMR spectra were consistent with the structure.

7-[D-(-)-α-aminophenylacetamido]-3-(thiazol-5-yl)carbonylthiomethyl-3-cephem-4-carboxylic acid

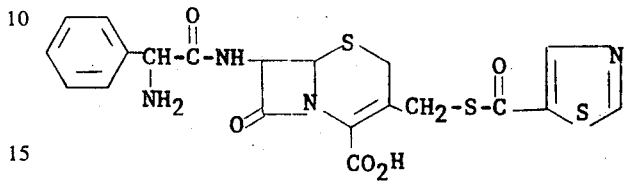

(BL-S602)

To a stirred slurry of 4.2 g. (0.0117 moles) of 7-amino-3-(thiazol-5-yl)carbonylthiomethyl-3-cephem-4-carboxylic acid in 115 ml. of dry methylene chloride was added successively 3.27 ml. (0.0234 moles) of triethylamine, 1.5 ml. (0.0117 moles) of N,N-dimethylaniline and 4.4 ml. (0.0351 moles) of trimethylchlorosilane. After being refluxed for 0.5 hour a clear brown solution resulted. It was cooled to 5° and 2.66 g. (0.0128 moles) of D-(-)-2 phenylglycyl chloride hydrochloride was added. The resulting slurry was stirred for 2 hours letting the temperature rise to 25°. This was then added to 115 ml. of ice water. The resulting tan precipitate was stirred for 15 minutes at room temperature, filtered, washed with water, acetone and ether and dried in vacuo over phosphorus pentoxide yielding 4.0 g. of a tan solid (I). The layers of the filtrate of I were separated and the aqueous phase was cooled, layered with 50 ml. of ethyl acetate and adjusted with 10% sodium hydroxide to pH 4.5. The resulting white solid was removed by filtration, washed with water, acetone and ether and dried in vacuo over phosphorus pentoxide to give 203 mg. (solid II).

Solid I was purified by slurrying in 50 ml. of water and 50 ml. of ethyl acetate and acidifying to pH 1.5 with 6 N hydrochloric acid. It was stirred for 15 minutes and the insoluble material was removed by filtration. The pH of the filtrate was adjusted with 10% sodium hydroxide to 4.5. A cloudy solution resulted, which was concentrated to a smaller volume until a tan solid precipitated. It was stirred at 5° for 15 minutes, filtered, washed with water, acetone and ether and dried in vacuo over phosphorus pentoxide to give 735 mg. (III). Combined II and III weighed 937 mg. (16%). Infrared and NMR spectra were consistent with the title structure.

Analysis: Calcd. for: $C_{20}H_{18}N_4O_5S_3 \cdot H_2O$: C, 47.25; H, 3.95; N, 11.02. Found: C, 46.58; H, 3.94; N, 10.81.

C. 4-methylthiazole-2-thiocarboxylic acid dicyclohexylamine salt

A mixture of 10 g. (0.07 moles) of 4-methyl-2-carboxythiazole and 50 ml. of thionyl chloride was refluxed for 22 hours and stirred for 72 hours at room temperature. The reaction mixture was concentrated under reduced pressure to a yellow oil which was flushed 2 times with methylene chloride. This acid chloride was slurried in 10 ml. of benzene. Not all went in solution and the insoluble material was removed by filtration. The benzene filtrate was added dropwise to a stirred, cooled and filtered solution of 15.4 g. (0.14 mole) of hydrated sodium sulfhydrate in 158 ml. of ethanol and 17.5 ml. of water at such a rate as to keep the temperature of the mixture at 10°–15°. After the addition was completed, the reaction mixture was stirred for 40 minutes at 5°–10° C. Most of the ethanol was removed under reduced pressure and the residue was dissolved in 90 ml. of water. The pH of the solution was lowered to 2.8 by addition of 6N hydrochloric acid and was maintained there while the mixture was extracted with 5 × 100 ml. of ethyl acetate. The extracts were combined, washed with ice water, dried over magnesium sulfate, filtered and evaporated to dryness to give a reddish solid. This was weighed, redissolved in 50 ml. of hot ethyl acetate and one equivalent of dicyclohexylamine was added. After a small amount of ether was added, crystals precipitated. After cooling for 1 hour they were removed by filtration, washed with ether and dried under high vacuum to give 10.81 g. (45.5%) of a yellow solid. NMR spectrum was consistent with the desired material.

Analysis: Calcd. for: $C_{17}H_{28}N_2S_2O$: C, 59.95; H, 8.29; N, 8.23. Found: C, 59.74; H, 8.44; N, 7.94.

4-methylthiazole-2-thiocarboxylic acid 10.0 g. (0.0294 mole) of 4-methyl-2-thiocarboxylic acid dicyclohexylamine salt, dissolved in 150 ml. of water and 150 ml. of ethyl acetate, was cooled and acidified with 6N hydrochloric acid to pH 2.2. The layers were separated and the aqueous phase was extracted with 150 ml. of ethyl acetate. The combined organic phases were dried over magnesium sulfate, filtered and evaporated under reduced pressure, yielding 3.1 g. (70%) of a red solid. Infrared spectrum was consistent with the desired material.

7-amino-3-(4-methylthiazol-2-yl)carbonylthiomethyl-3-cephem-4-carboxylic acid

To a stirred solution of 5.4 g. (0.02 mole) of 7-aminocephalosporanic acid and 3.36 g. (0.04 mole) of sodium bicarbonate in 120 ml. of aqueous phosphate buffer (pH 6.4) was added 3.1 g. (0.02 mole) of 4-methylthiazole-2-thiolcarboxylic acid. The mixture was stirred in a nitrogen atmosphere and heated to 50°. The pH was adjusted from 7.0 to 6.5 with 42% phosphoric acid. A crystalline solid started to precipitate. After 5 hours at 50° the reaction mixture was cooled to 20°. The precipitated solid was collected by filtration, washed with water and acetone and dried in vacuo over phosphorous pentoxide 3.75 g. of crystalline yellow solid. Yield = 50.5% NMR spectrum was consistent with the structure of the title product.

7-[D-α-aminophenylacetamido]-3-(4-methylthiazol-2-yl)carbonylthiomethyl-3-cephem-4-carboxylic acid To a stirred slurry of 3.7 g. (0.01 mole) of 7-amino-3-(4-methylthiazole-2-yl)carbonylthiomethyl-3-cephem-4-carboxylic acid in 100 ml. of dry methylene chloride were added 2.8 ml. (0.02 mole) of triethylamine, 1.27 ml. (0.01 mole) of N,N-dimethylaniline and 3.75 ml. (0.03 mole) of trimethylchlorosilane. The yellow solution was heated under reflux for 40 minutes and was then cooled to 3° and treated with vigorous stirring with 2.27 g. (0.011 mole) of D-phenylglycyl chloride hydrochloride. The resulting slurry was stirred for 2 hours letting the temperature slowly rise to 20°. A slightly yellow solution resulted. This was added to 100 ml. of ice water and the precipitated product was collected by filtration and washed with water, acetone and ether. The resulting solid (3.5 g.) was slurried in 15 ml. of water and 15 ml. of acetone, cooled to 5° and acidified with 6N hydrochloric acid to pH 1.5. Most of it went in solution. This mixture was treated with Norite and Celite, filtered and the filtrate cooled and adjusted with 10% aqueous sodium hydroxide to pH 4.5. A colorless solid precipitated. It was removed by filtration, washed with water and dried in high vacuum for 15 hours. A colorless solid resulted; 2.1 g. (41.5% yield). Infrared spectrum and NMR spectrum were consistent with the proposed structure.

Analysis: Calcd. for: $C_{21}H_{20}N_4O_5S_3.H_2O$: C, 48.26; H, 4.24; N, 10.72. Found: C, 47.75; H, 4.35; N, 10.68.

D. 4,5-Dimethylthiazole-2-thiolcarboxylic acid dicyclohexylamine salt

To a slurry of 19.0 g. (0.121 mole) of 4,5-dimethylthiazole-2-carboxylic acid in 250 ml. of dry methylene chloride was added over 1 hour 10.3 ml. (0.121 mole) of oxalyl chloride. The reaction mixture was stirred at room temperature for 1 hour and was refluxed for 2 hours. The small amount of insoluble material was removed by filtration and the filtrate was concentrated under reduced pressure to a yellow oil. Infrared spectrum indicated this to be the desired acid chloride. This was added dropwise to a stirred and cooled solution of 26.4 g. (0.24 mole) of hydrated sodium sulfhydrate in 275 ml. of ethanol and 30 ml. of water at such a rate as to keep the temperature of the mixture at 10°–15°. After the addition was completed, the reaction mixture was stirred for 40 minutes at 5°–10°. Then most of the ethanol was removed under reduced pressure and the residue was dissolved in 150 ml. of water. The pH of the solution was lowered to 2.5 with 6N hydrochloric acid and was maintained there, while the mixture was extracted with 5 × 100 ml. of ethyl acetate. The extracts were combined, washed with ice water, dried over magnesium sulfate, filtered and evaporated to dryness to give 10.6 g. of a reddish solid. It was dissolved in 200 ml. of hot ethanol and 7.5 ml. of dicyclohexylamine were added. Bright yellow crystals resulted. The mixture was cooled at 5° for 1 hour. Then the precipitate was removed by filtration, washed with ether and dried under high vacuum to give 11.75 g. (27%) of a yellow solid. NMR spectrum was consistent with the desired material.

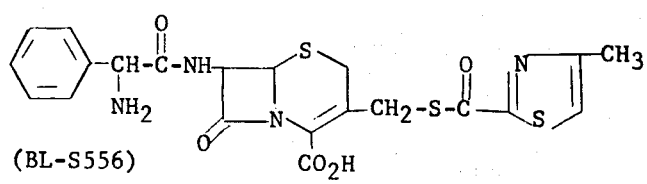

(BL-S556)

Analysis: Calcd. for: $C_{18}H_{30}N_2OS_2$: Found: C, 60.97; H, 8.54; N, 7.92. Found: C, 60.93; H, 8.67; N, 7.76.

4,5-Dimethylthiazole-2-thioicarboxylic acid 11.7 g. (0.033 mole) of 4,5-dimethylthiazole-2-thiolcarboxylic acid dicyclohexylamine salt, dissolved in 175 ml. of water and 175 ml. of ethyl acetate, was cooled and acidified with 6N hydrochloric acid to pH 2.2. The layers were separated and the aqueous phase was extracted with 2 × 75 ml. of ethyl acetate. The combined organic phases were dried over magnesium sulfate, filtered and evaporated under reduced pressure yielding 4.6 g. (80%) of a red solid. Infrared spectrum was consistent with the desired material.

7-Amino-3-(4,5-dimethylthiazol-2-yl)carbonylthiomethyl-3-cephem-4-carboxylic acid To a stirred solution of 7.22 g. (0.0265 mole) of 7-aminocephalosporanic acid and 4.45 g. (0.053 mole) of sodium bicarbonate in 160 ml. of aqueous phosphate buffer (ph 6.4) was added 4.6 g. (0.0265 mole) of 4,5-dimethylthiazole-2-thiolcarboxyic acid. The mixture was stirred in a nitrogen atmosphere and heated to 50°. The pH was adjusted from 7.0 to 6.5 with 42% phosphoric acid. A crystalline solid started to precipitate. After 5 hours at 50° the reaction mixture was cooled to 20°. The precipitated solid was collected by filtration, washed with water and acetone and dried in vacuo over phosphorus pentoxide to provide 4.55 g. of a tan crystalline material. Yield = 45%. NMR spectrum was consistent with structure.

7-[D-α-aminophenylacetamido]-3-(4,5-dimethylthiazol-2-yl)carbonylthiomethyl-3-cephem-4-carboxylic acid and adjusted with 10% aqueous sodium hydroxide to pH 4.5. A tan crystalline material precipitated. It was removed by filtration, washed with acetone and ether and dried in high vacuum. A tan crystalline solid resulted; 850 mg. (13.8% yield). Infrared spectrum and NMR spectrum were consistent with the title structure.

Analysis: Calcd. for: $C_{22}H_{22}N_4O_5S_3.H_2O$: C, 49.25; H, 4.52; N, 10.40. Found: C, 49.51; H, 4.63; N, 10.28.

E. 2-Methylthiazole-4-thiolcarboxylic acid, potassium salt

A solution of potassium hydrogen sulfide in ethanol was prepared by dissolving potassium metal (5.9 g., 0.15 moles) in 500 ml. of absolute ethanol under an atmosphere of dry nitrogen, cooling to 5° C., and saturating the solution with hydrogen sulfide. 2-methylthiazole-4-carbonyl chloride (12.3 g., 0.076 moles) was added portionwise at 5° C. under an atmosphere of dry nitrogen to the freshly prepared potassium hydrogen sulfide solution. When the addition was complete, the mixture was allowed to come to room temperature and stirred for 2 hours. The mixture was then evaporated under reduced pressure and the residue was slurried with ether and collected by filtration.

This material was extracted with 800 ml. of refluxing ethanol and the ethanol solution was then evaporated to a small volume. Ether was added to turbidity and it was left to cool. The solid 2-methylthiazole-4-thiolcarboxylic acid potassium salt was collected by filtration and dried. The yield was 9.8 g. (66%) with m.p. 238°–244° C.

A sample crystallized twice from ethanol had m.p. 243°–246° C.

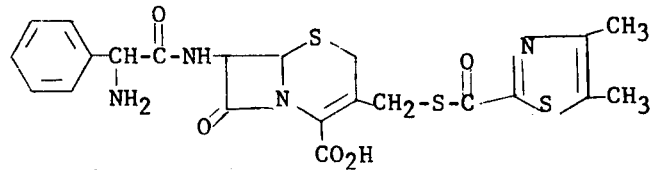

(BL-S587)

To a stirred slurry of 4.55 g. (0.0119 mole) of 7-amino-3-(4,5-dimethylthiazol-2-yl)carbonylthiomethyl-3-cephem-4-carboxylic acid in 120 ml. of dry methylene chloride were added 3.34 ml. (0.022 mole) of triethylamine, 1.51 ml. (0.0119 moles) of N,N-dimethylaniline and 4.45 ml. (0.0382 mole) of trimethylchlorosilane. The yellow solution was heated under reflux for 40 minutes and was then cooled to 3° and treated with vigorous stirring with 2.7 g. (0.0119 mole) of D-phenylglycyl chloride hydrochloride. The resulting slurry was stirred for 2 hours letting the temperature slowly rise to 20°. A slightly yellow suspension resulted. This was added to 120 ml. of ice water and the precipitated product was collected by filtration and washed with water, acetone and ether. The resulting tan solid (4.0 g.) was slurried in 10 ml. of water and 10 ml. of ethyl acetate, cooled to 5° and acidified with 6N hydrochloric acid to pH 1.5. Not all went in solution. It was stirred at 5° for 30 minutes. The insoluble material was removed by filtration and the filtrate was cooled Analysis: Calcd. for: $C_5H_4KNOS_2$: C, 30.43; H, 2.04; N, 7.10. Found: C, 30.35; H, 2.04; N, 6.93.

7-Amino-3-(2-methylthiazol-4-yl)carbonylthiomethyl-3-cephem-4-carboxylic acid

To a stirred suspension of 6.8 g. (0.025 mole) of 7-aminocephalosporanic acid and 2.1g. (0.025 mole) of sodium bicarbonate in 150 ml. of aqueous phosphate buffer (pH 6.4) was added 4.92 g. (0.025 mole) of 2-methylthiazole-4-thiolcarboxylic acid potassium salt. The mixture was stirred in a nitrogen atmosphere and heated to 50°. The pH was adjusted from 7.0 to 6.5 with 42% phosphoric acid. A tan solid started to precipitate. After 5 hours at 50° the reaction mixture was cooled to 20°. The solid was collected by filtration, washed with water, acetone and ether and dried in vacuo over phosphorous pentoxide to provide 4.5 g. of a tan solid. Yield = 48%. NMR spectrum was consistent with structure.

7-[D-α-aminophenylacetamido]-3-(2-methylthiazol-4-yl)carbonylthiomethyl-3-cephem-4-carboxylic acid

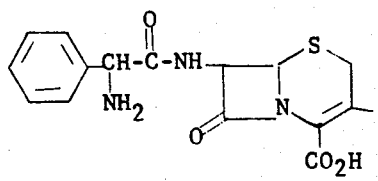

(BL-S607)

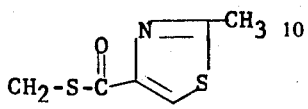

To a stirred slurry of 4.2 g. (0.0117 mole) of 7-amino-3-(2-methylthiazol-4-yl)carbonylthiomethyl-3-cephem-4-carboxylic acid in 115 ml. of dry methylene chloride were added 3.27 ml. (0.0234 mole) of triethylamine, 1.5 ml. (0.0117 mole) of N,N-dimethylaniline and 4.4 ml. (0.0351 mole) of trimethylchlorosilane. The orange solution was heated under reflux for 40 minutes and was then cooled to 5° and treated with vigorous stirring with 2.66 g. (0.0128 mole) of D-phenylglycyl chloride hydrochloride. The resulting slurry was stirred for 2 hours letting the temperature slowing rise to 20°. The resulting cloudy solution was added to 120 ml. of cold water and the precipitated product was collected by filtration and washed with water, acetone and ether. The resulting tan solid (4.0 g.) was slurried in 10 ml. of water and 10 ml. of ethyl acetate, cooled to 5° and acidified with 6N hydrochloric acid to pH 1.5. Not all went in solution. It was stirred for 15 minutes at room temperature. The insoluble material was removed by filtration and the filtrate was cooled and adjusted with 10% aqueous sodium hydroxide to pH 4.5. A tan solid precipitated. It was removed by filtration, washed with water, acetone and ether and dried in high vacuum. A tan solid resulted. The filtrate was concentrated to a small volume yielding more product. Combined weight, 1.25 g.; yield = 21%. Infrared spectrum and NMR spectrum were consistent with the title product.

Analysis: Calcd. for: $C_{21}H_{20}N_4O_5S_3 \cdot 2H_2O$: C, 46.65; H, 4.47; N, 10.35. Found: C, 46.97; H, 4.13; N, 10.30.

We claim:

1. A compound having the D-configuration in the 7-sidechain and the formula

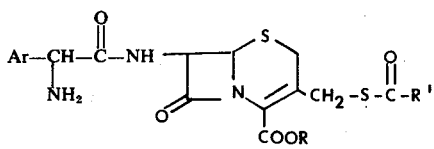

wherein Ar is phenyl, 2-thienyl or 3-thienyl; R is hydrogen, pivaloyloxymethyl, acetoxymethyl, methoxymethyl, acetonyl or phenacyl; and R' is 5-methyl-2-thiazolyl; or a pharmaceutically acceptable salt thereof.

2. An acid having the D-configuration in the 7-sidechain and the formula

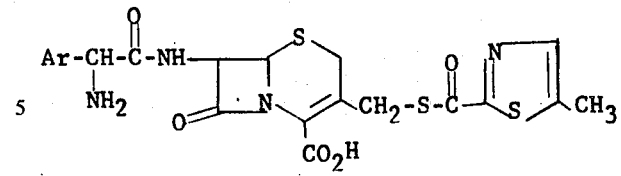

wherein Ar is phenyl, 2-thienyl or 3-thienyl; or a pharmaceutically acceptable salt thereof.

3. An acid of claim 1 having the formula

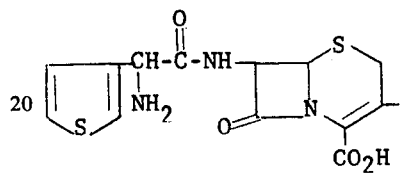

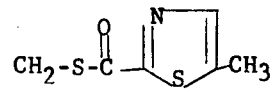

or a pharamaceutically acceptable salt thereof.

4. The sodium salt of the acid of claim 1.
5. The potassium salt of the acid of claim 1.
6. The zwitterion form of the acid of claim 1.
7. A pharmaceutically acceptable acid addition salt of the acid of claim 1.
8. The pivaloyloxymethyl ester of the acid of claim 1 in which Ar is 3-thienyl.
9. The acetoxymethyl ester of the acid of claim 1 in which Ar is 3-thienyl.
10. The methoxymethyl ester of the acid of claim 1 in which Ar is 3-thienyl.
11. The acetonyl ester of the acid of claim 1 in which Ar is 3-thienyl.
12. The phenacyl ester of the acid of claim 1 in which Ar is 3-thienyl.
13. An acid of claim 2 having the formula

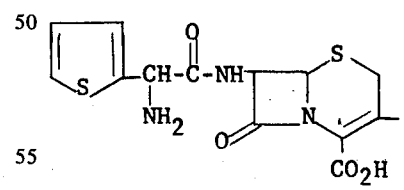

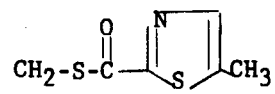

or a pharmaceutically acceptable salt thereof.

14. The sodium salt of the acid of claim 13.
15. The potassium salt of the acid of claim 13.
16. The zwitterion form of the acid of claim 13.

17. A pharmaceutically acceptable acid addition salt of the acid of claim 13.

18. The pivaloyloxymethyl ester of the acid of claim 1 in which Ar is 2-thienyl.

19. The acetoxymethyl ester of the acid of claim 1 in which Ar is 2-thienyl.

20. The methoxymethyl ester of the acid of claim 1 in which Ar is 2-thienyl.

21. The acetonyl ester of the acid of claim 1 in which Ar is 2-thienyl.

22. The phenacyl ester of the acid of claim 1 in which Ar is 2-thienyl.

23. An acid having the D-configuration in the 7-sidechain and the formula

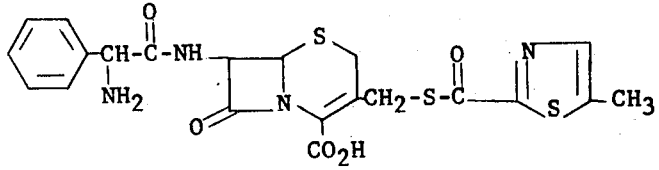

or a pharmaceutically acceptable salt thereof.

24. The sodium salt of the acid of claim 23.

25. The potassium salt of the acid of claim 23.

26. The zwitterion form of the acid of claim 23.

27. A pharmaceutically acceptable acid addition salt of the acid of claim 23.

28. The pivaloyloxymethyl ester of the acid of claim 1 in which Ar is phenyl.

29. The acetoxymethyl ester of the acid of claim 1 in which Ar is phenyl.

30. The methoxymethyl ester of the acid of claim 1 in which Ar is phenyl.

31. The acetonyl ester of the acid of claim 1 in which Ar is phenyl.

32. The phenacyl ester of the acid of claim 1 in which Ar is phenyl.

\* \* \* \* \*